(12) United States Patent
Janowski

(10) Patent No.: US 9,186,184 B2
(45) Date of Patent: Nov. 17, 2015

(54) SPINAL FIXATION SYSTEM AND METHOD

(75) Inventor: Brian P. Janowski, Marquette, MI (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 0 days.

(21) Appl. No.: 13/366,117

(22) Filed: Feb. 3, 2012

(65) Prior Publication Data

US 2012/0209332 A1    Aug. 16, 2012

Related U.S. Application Data

(60) Provisional application No. 61/442,617, filed on Feb. 14, 2011.

(51) Int. Cl.
*A61B 17/70* (2006.01)
*A61B 19/00* (2006.01)

(52) U.S. Cl.
CPC .......... *A61B 17/7038* (2013.01); *A61B 17/7041* (2013.01); *A61B 17/7082* (2013.01); *A61B 17/7085* (2013.01); *A61B 2019/307* (2013.01)

(58) Field of Classification Search
CPC ........... A61B 17/7041; A61B 17/7076; A61B 17/7037; A61B 17/7035; A61B 17/7083; A61B 17/8083
USPC ................ 606/86 A, 99, 264–279
See application file for complete search history.

(56) References Cited

U.S. PATENT DOCUMENTS

| | | | | |
|---|---|---|---|---|
| 4,653,481 A | * | 3/1987 | Howland et al. | 606/261 |
| 5,030,220 A | * | 7/1991 | Howland | 606/261 |
| 5,584,831 A | * | 12/1996 | McKay | 606/86 A |
| 5,725,528 A | * | 3/1998 | Errico et al. | 606/266 |
| 5,733,285 A | * | 3/1998 | Errico et al. | 606/278 |
| 5,735,851 A | * | 4/1998 | Errico et al. | 606/266 |

(Continued)

FOREIGN PATENT DOCUMENTS

| | | |
|---|---|---|
| BR | 0600528-4 | 10/2007 |
| EP | 1638472 | 11/2012 |

(Continued)

OTHER PUBLICATIONS

Website, Medicrea, Products, Thoraco-Lumbar fusion, http://www.Medicrea.com/version-US/produit-thoracolumbar-fixation.php?Ig=us&rub=18partie=3&55partie=0, accessed Jan. 17, 2012, 3 pages.

(Continued)

*Primary Examiner* — Eduardo C Robert
*Assistant Examiner* — Jacqueline Johanas
(74) *Attorney, Agent, or Firm* — Fitch, Even, Tabin & Flannery LLP

(57) ABSTRACT

A spinal fixation system is provided that, in one form, comprises a pedicle screw assembly having a coupling device with an elongate member for guiding a fixation element, such as a spinal rod, into the coupling device and a lock device for fixing the spinal rod to the coupling device. The pedicle screw assembly may be passed through a small incision and connected to a vertebral bone. By connecting a second pedicle screw assembly to a second vertebral bone, the elongate members of the pedicle screw assemblies provide guideposts for directing the spinal rod subcutaneously between the pedicle screw assemblies and into the coupling devices thereof.

14 Claims, 29 Drawing Sheets

(56) References Cited

U.S. PATENT DOCUMENTS

| | | | |
|---|---|---|---|
| 5,800,435 A * | 9/1998 | Errico et al. | 606/261 |
| 6,050,997 A | 4/2000 | Mullane | |
| 6,123,706 A * | 9/2000 | Lange | 606/264 |
| 6,248,104 B1 * | 6/2001 | Chopin et al. | 606/267 |
| 6,254,602 B1 * | 7/2001 | Justis | 606/272 |
| 6,267,765 B1 * | 7/2001 | Taylor et al. | 606/86 A |
| 6,371,957 B1 * | 4/2002 | Amrein et al. | 606/272 |
| 6,554,831 B1 * | 4/2003 | Rivard et al. | 606/253 |
| 6,786,907 B2 * | 9/2004 | Lange | 606/250 |
| 6,887,242 B2 * | 5/2005 | Doubler et al. | 606/274 |
| 7,163,539 B2 | 1/2007 | Abdelgany et al. | |
| 7,166,108 B2 * | 1/2007 | Mazda et al. | 606/305 |
| 7,344,537 B1 * | 3/2008 | Mueller | 606/278 |
| 7,731,734 B2 * | 6/2010 | Clement et al. | 606/246 |
| 7,753,939 B2 * | 7/2010 | Ritland | 606/264 |
| 7,763,057 B2 | 7/2010 | Abdelgany et al. | |
| 7,789,897 B2 * | 9/2010 | Sanders | 606/278 |
| 7,846,093 B2 * | 12/2010 | Gorek et al. | 600/206 |
| 8,021,396 B2 * | 9/2011 | Winslow et al. | 606/264 |
| 8,043,343 B2 * | 10/2011 | Miller et al. | 606/279 |
| 8,057,518 B2 * | 11/2011 | Frasier et al. | 606/267 |
| 8,083,773 B2 * | 12/2011 | Durrani | 606/259 |
| 8,162,990 B2 * | 4/2012 | Potash et al. | 606/266 |
| 8,221,457 B2 * | 7/2012 | Delecrin et al. | 606/246 |
| 8,221,470 B2 * | 7/2012 | Kumar et al. | 606/265 |
| 8,226,656 B2 * | 7/2012 | McBride | 606/86 A |
| 8,246,623 B2 * | 8/2012 | Peultier et al. | 606/86 A |
| 8,308,772 B2 | 11/2012 | Clement et al. | |
| 8,308,775 B2 | 11/2012 | Clement et al. | |
| 8,333,770 B2 * | 12/2012 | Hua | 606/86 A |
| 8,470,001 B2 * | 6/2013 | Trautwein et al. | 606/264 |
| 8,617,216 B2 * | 12/2013 | Brumfield | 606/266 |
| 8,894,690 B2 * | 11/2014 | Ludwig et al. | 606/264 |
| 2002/0169450 A1 * | 11/2002 | Lange | 606/61 |
| 2003/0023240 A1 * | 1/2003 | Amrein et al. | 606/61 |
| 2003/0028191 A1 * | 2/2003 | Shluzas | 606/61 |
| 2003/0045874 A1 * | 3/2003 | Thomas, Jr. | 606/61 |
| 2003/0073996 A1 * | 4/2003 | Doubler et al. | 606/61 |
| 2003/0093078 A1 * | 5/2003 | Ritland | 606/73 |
| 2004/0064140 A1 | 4/2004 | Taylor et al. | |
| 2004/0254577 A1 * | 12/2004 | Delecrin et al. | 606/61 |
| 2005/0010215 A1 * | 1/2005 | Delecrin et al. | 606/61 |
| 2005/0096654 A1 * | 5/2005 | Lin | 606/61 |
| 2005/0171537 A1 * | 8/2005 | Mazel et al. | 606/61 |
| 2005/0192571 A1 | 9/2005 | Abdelgany | |
| 2005/0192572 A1 | 9/2005 | Abdelgany et al. | |
| 2005/0192579 A1 * | 9/2005 | Jackson | 606/72 |
| 2005/0228382 A1 * | 10/2005 | Richelsoph et al. | 606/61 |
| 2006/0079892 A1 * | 4/2006 | Roychowdhury et al. | 606/61 |
| 2006/0079899 A1 * | 4/2006 | Ritland | 606/61 |
| 2006/0083603 A1 * | 4/2006 | Jackson | 411/386 |
| 2006/0111712 A1 * | 5/2006 | Jackson | 606/61 |
| 2006/0167455 A1 | 7/2006 | Clement et al. | |
| 2006/0184178 A1 * | 8/2006 | Jackson | 606/99 |
| 2006/0229606 A1 | 10/2006 | Clement et al. | |
| 2007/0016190 A1 | 1/2007 | Martinez et al. | |
| 2007/0032162 A1 * | 2/2007 | Jackson | 446/1 |
| 2007/0072493 A1 | 3/2007 | Sournac et al. | |
| 2007/0078460 A1 * | 4/2007 | Frigg et al. | 606/61 |
| 2007/0093831 A1 | 4/2007 | Abdelgany et al. | |
| 2007/0093832 A1 | 4/2007 | Abdelgany | |
| 2007/0100339 A1 | 5/2007 | Clement et al. | |
| 2007/0106123 A1 * | 5/2007 | Gorek et al. | 600/210 |
| 2007/0149973 A1 | 6/2007 | Clement et al. | |
| 2007/0233066 A1 * | 10/2007 | Rezach | 606/61 |
| 2007/0270810 A1 * | 11/2007 | Sanders | 606/61 |
| 2008/0091213 A1 * | 4/2008 | Jackson | 606/99 |
| 2008/0312696 A1 * | 12/2008 | Butters et al. | 606/264 |
| 2009/0030457 A1 | 1/2009 | Janowski et al. | |
| 2009/0062864 A1 * | 3/2009 | Ludwig et al. | 606/301 |
| 2009/0222044 A1 * | 9/2009 | Gorek | 606/279 |
| 2009/0222045 A1 * | 9/2009 | Gorek | 606/279 |
| 2009/0270916 A1 * | 10/2009 | Ramsay et al. | 606/246 |
| 2010/0168796 A1 * | 7/2010 | Eliasen et al. | 606/264 |
| 2010/0241172 A1 * | 9/2010 | Biyani et al. | 606/279 |
| 2010/0249798 A1 | 9/2010 | Sournac et al. | |
| 2010/0292739 A1 * | 11/2010 | Schwab | 606/305 |
| 2011/0015679 A1 | 1/2011 | Fiere et al. | |
| 2011/0112581 A1 | 5/2011 | Clement | |
| 2011/0245877 A1 * | 10/2011 | Pisharodi | 606/268 |
| 2011/0282400 A1 * | 11/2011 | Jackson | 606/305 |
| 2013/0072991 A1 * | 3/2013 | Rathbun | 606/305 |

FOREIGN PATENT DOCUMENTS

| | | |
|---|---|---|
| EP | 2445427 | 3/2013 |
| FR | 2956803 | 9/2002 |
| FR | 2867375 | 9/2005 |
| WO | 2005000136 | 1/2005 |
| WO | 2009011929 | 1/2009 |
| WO | 2010150140 | 12/2010 |
| WO | 2012029025 | 3/2012 |
| WO | 2013014589 | 1/2013 |

OTHER PUBLICATIONS

Website, YouTube, PASS MIS Technique 4 Level Trauma, http://www.youtube.com/watch?v=ofm3w0qy6hw, accessed Jan. 27, 2012, 2 pages, only 2 pages of screen shot considered, content of video not considered /J.J./ Oct. 9, 2013.

* cited by examiner

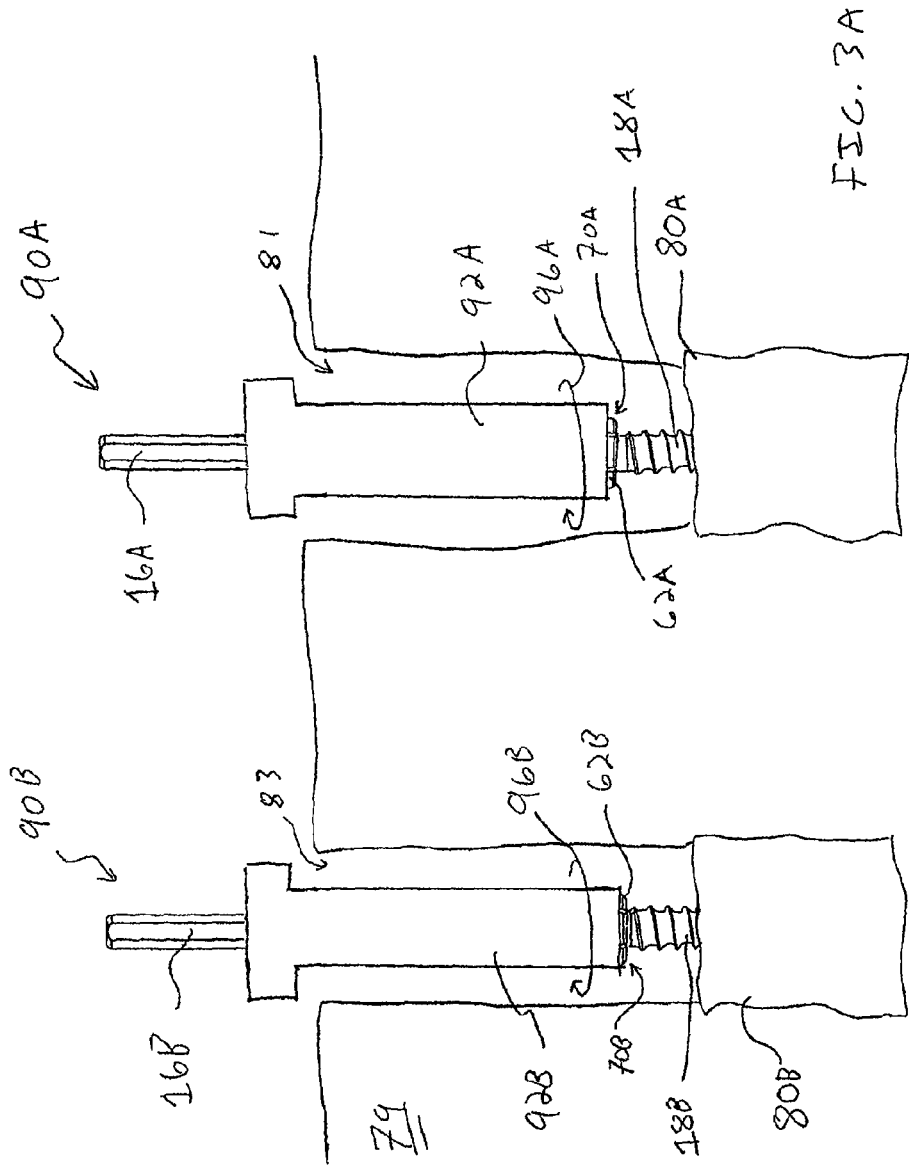

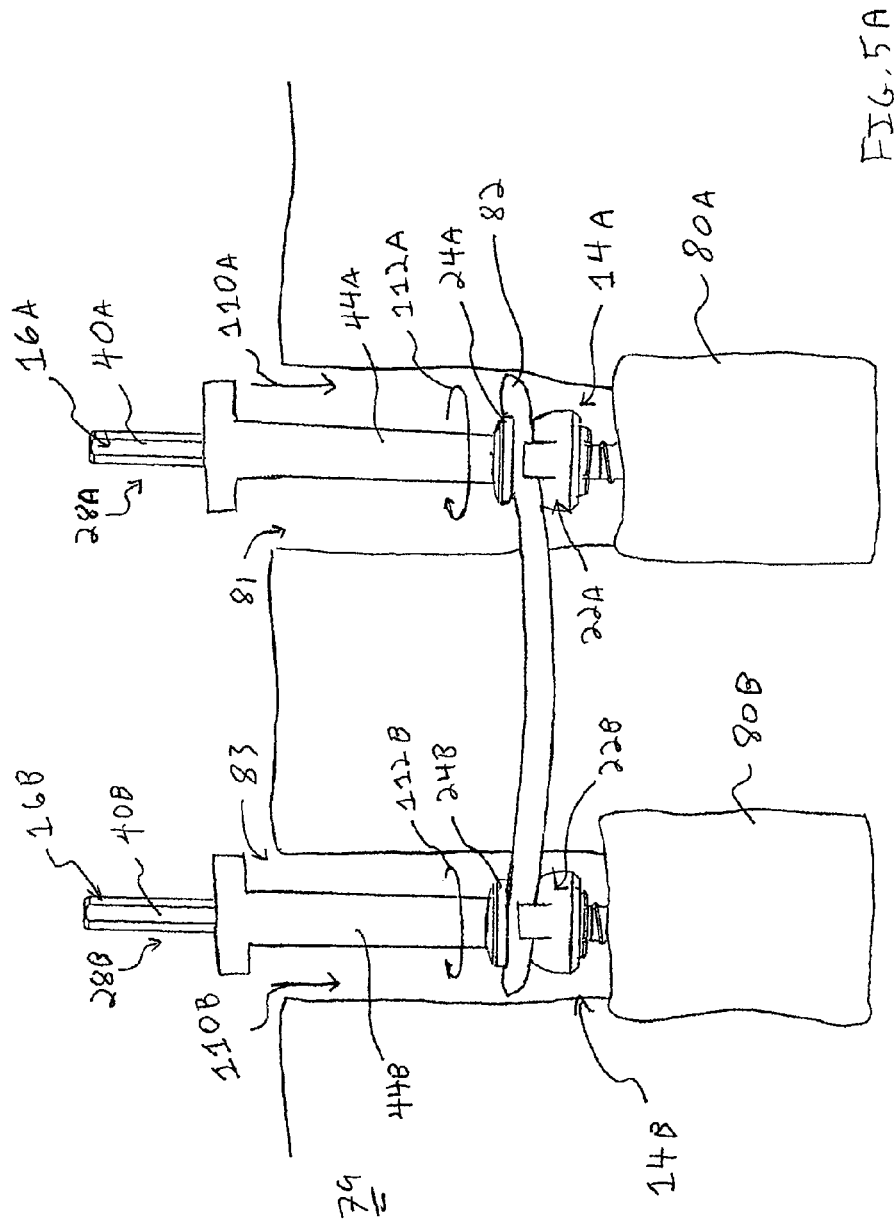

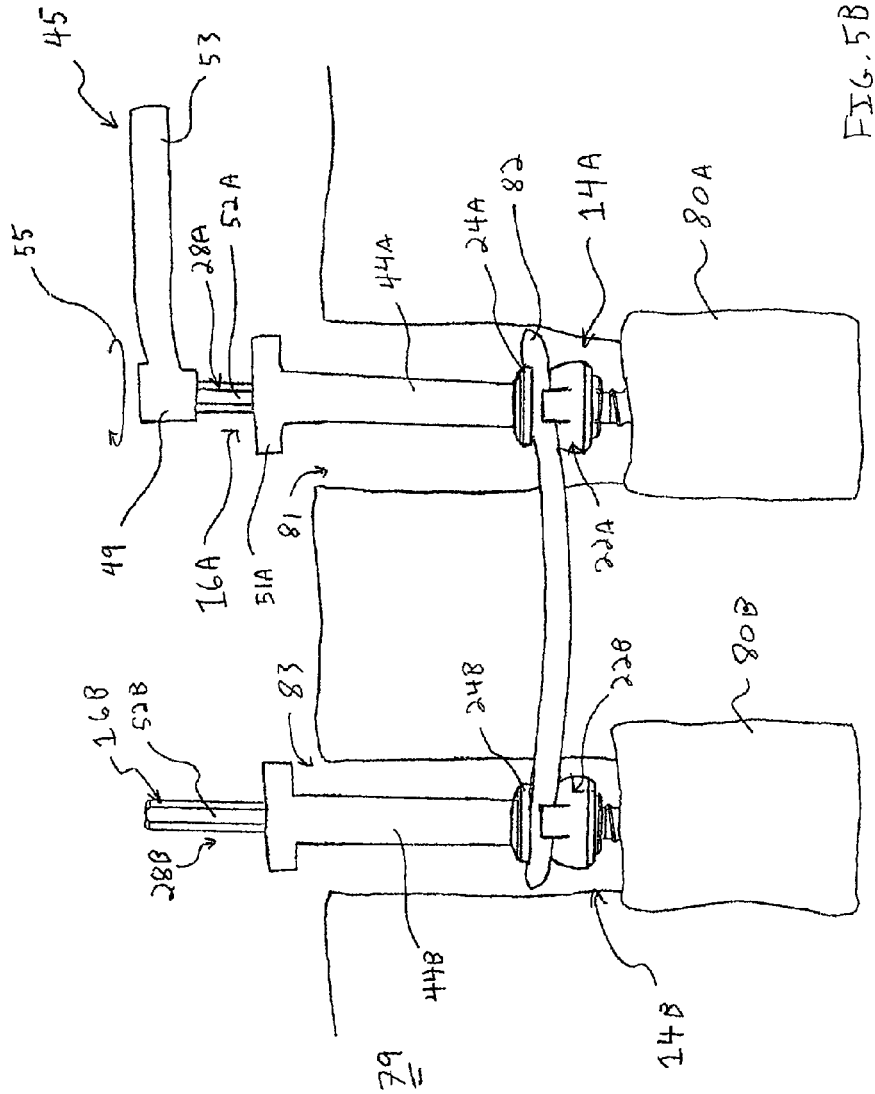

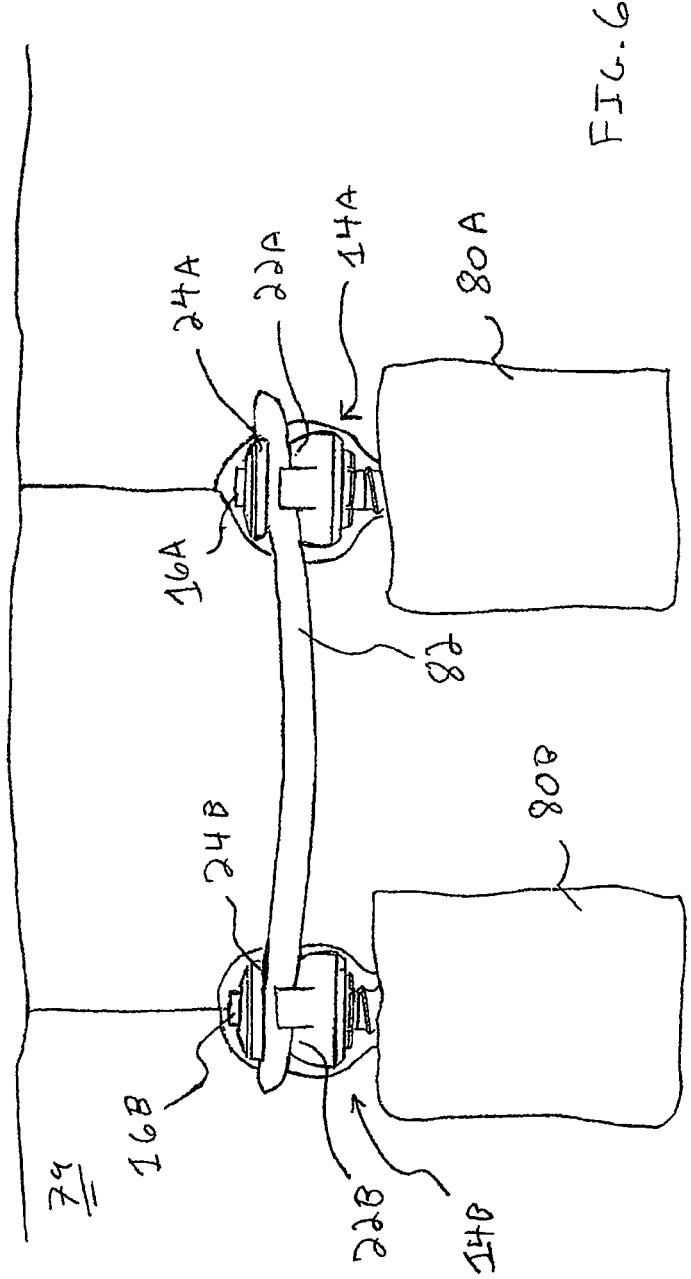

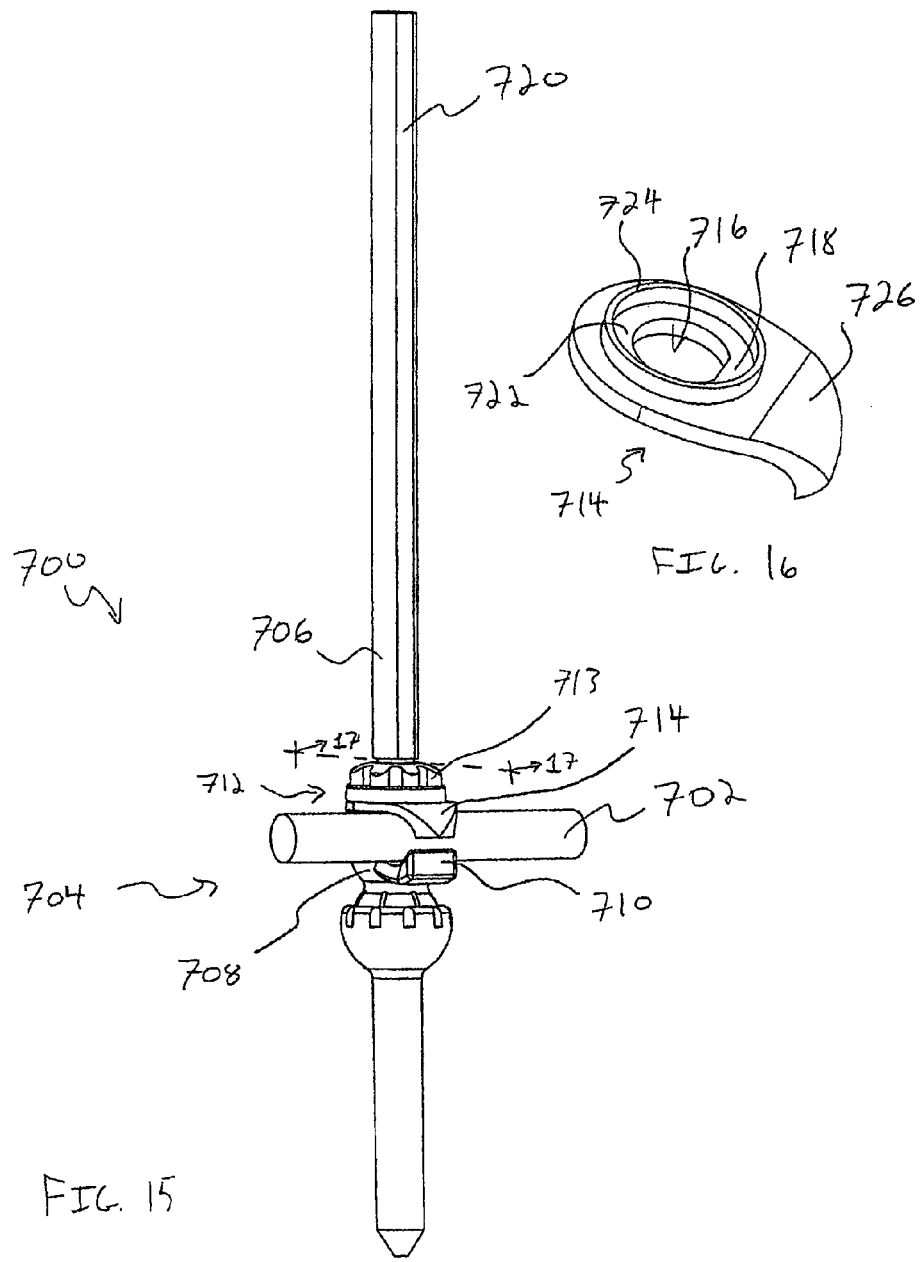

SPINAL FIXATION SYSTEM AND METHOD

CROSS-REFERENCE TO RELATED APPLICATION

This application claims the benefit of U.S. Provisional Patent Application No. 61/442,617, filed Feb. 14, 2011, which is hereby incorporated by reference in its entirety.

FIELD OF THE INVENTION

This invention relates to bone fixation systems and, more particularly, to spinal fixation systems and methods used in minimally invasive procedures.

BACKGROUND OF THE INVENTION

Existing minimally invasive surgical techniques include inserting rodding systems through a small incision at the surface of the skin. These surgical techniques often use some form of an extender tube placed over the yoke of the pedicle screw to manipulate positioning of the yoke. The extender tube is also used to pass instruments for persuading the rod, inserting and advancing a locking cap, applying a counter-torque during cap locking, and removing or releasing hardware. These yoke extender tubes typically have slots in their sides to serve as a window to pass the spinal rod under the skin and through the yoke. Utilizing these surgical systems often becomes a complex task involving a multitude of surgical tools that are repeatedly connected and disconnected to achieve the desired surgical task.

SUMMARY OF THE INVENTION

In accordance with one aspect of the present invention, a spinal fixation system is provided that permits a spinal rod to be secured to a pair of pedicle screw assemblies during minimally invasive surgery without the use of pedicle screw yoke extender tubes. Instead, the spinal fixation system comprises two or more pedicle screw assemblies each having an upstanding elongate member for directing the spinal rod as the spinal rod is advanced subcutaneously and secured with the pedicle screw assemblies. The elongate member may be solid, cannulated, or have other cross-sectional configurations, although a solid cross-section permits the profile of the elongate member to be minimized. A distal end of the spinal rod is advanced transversely relative to the elongate members with contact between the spinal rod and the elongate members providing tactile feedback that the spinal rod is positioned adjacent the pedicle screw assemblies. The spinal rod is free to travel along, away from, toward, and around the elongate members such that the spinal rod can be maneuvered to avoid tissues and/or boney structures while seating the spinal rod on the pedicle screw assemblies. In this manner, the spinal rod may be guided into position on the pedicle screw assemblies without having to fit the spinal rod through slots of yoke extender tubes, as in some traditional approaches.

In another aspect, a spinal fixation system is provided having a pedicle screw assembly with an open seat for receiving a spinal rod, rather than a yoke as in some traditional pedicle screw assemblies. Whereas a traditional pedicle screw assembly yoke has a U-shape with walls that restrict insertion and removal of a spinal rod to generally linear paths between the yoke walls, the open seat of the instant pedicle screw assembly allows the spinal rod to be positioned on the seat using a range of substantially unrestricted insertion paths. In one form, the seat comprises an arm disposed at the base of an elongate member with a planar seating surface for receiving the spinal rod. The spinal rod may be positioned on the seating surface using a number of different paths, including a vertical path generally downward along the associated elongate member, an oblique path generally downward and at an angle to the elongate member, and a horizontal path generally perpendicular to the elongate member. The ability of the seat to accommodate different insertion paths of the spinal rod provides greater flexibility to maneuver the spinal rod around tissues and/or boney structures during minimally invasive surgery. To fix the spinal rod on the seat, a locking cap is slid downward along the elongate member and engaged with a lower portion of the elongate member. The locking cap clamps the spinal rod against the seat and fixes the spinal rod relative to the associated pedicle screw assembly.

In accordance with another aspect of the present invention, a spinal fixation system comprises a pedicle screw assembly having a bone anchor, a coupling device connected to the bone anchor, and a lock device configured to secure a fixation element, such as a spinal rod, to the coupling device. The coupling device has an elongate member configured to guide the spinal rod onto the coupling device. Rather than pass tools and components through a cannula of a yoke extender tube, as in some minimally invasive surgical procedures, the tools and components of the spinal fixation system travel along exterior surfaces of the elongate members. In a preferred embodiment, the elongate member has an integrally releasable or break-away connection with the coupling device to permit the elongate member to be broken off after the spinal rod has been secured to the coupling device.

In another aspect, a spinal fixation system having a pedicle screw assembly and a spinal rod is provided that allows one-step fixation of the spinal rod relative to a vertebral bone. The pedicle screw assembly has a coupling device connected to a bone screw with an elongate member for guiding the spinal rod onto the coupling device. The coupling device has a seat for receiving the spinal rod, the seat preferably being in the form of a body having a curved surface, a flat surface, a ledge, an arm, or other configuration. The coupling device comprises a locking cap that travels along the elongate member and connects to a lower end of the elongate member to fix the spinal rod to the coupling device and substantially simultaneously fix the coupling device relative to the bone screw. In one preferred embodiment, the pedicle screw assembly has a ball and socket connection between the coupling device and the bone screw. Engaging the locking cap with the lower end of the elongate member fixes the ball and socket connection against movement and rigidly connects the spinal rod to the vertebral bone.

A method is also provided that permits a surgeon to visually align a spinal rod with one or more elongate members extending above a patient's skin before advancing the spinal rod through an incision and permits the surgeon to use outer surfaces of the one or more elongate members as guides while advancing the spinal rod subcutaneously. Initially, a small incision is made in a patient's skin and other tissues adjacent a pair of vertebral bones. A guide wire is inserted through each of the incisions into contact with a respective vertebral bone before serial dilators are passed over the guide wires and into contact with the vertebral bones. A tubular member may optionally be fit over the dilators and secured to the vertebral bones to form a working channel. A pair of bone screws and coupling devices connected thereto are advanced through the working channels and driven into engagement with the vertebral bones. The coupling devices have upstanding, elongate members sized to extend above the skin of the patient from within the working channels and permit the surgeon to visualize the location of the vertebral bones via the elongate members. The surgeon may consider the distance between the elongate members in determining the length of the spinal rod selected to secure the vertebral bones. Imaging devices, such as x-ray machines, or internal or external measuring devices may also be used to determine the length of the spinal rod desired to secure the vertebral bones. Further, the elongate members extending above the skin permit the surgeon to visually align the spinal rod with a desired path between the elongate members, e.g., the spinal rod is to travel on the left lateral side of both elongate members.

The method may further include using a rod inserter tool to advance a distal end portion of a spinal rod toward one of the vertebral bones through the associated working channel. The distal end of the spinal rod is advanced along an outer surface of the elongate member positioned in the working channel until reaching a seat of the coupling device which is disposed at the base of the elongate member. The distal end of the spinal rod may then be advanced beneath the skin and other tissues of the patient toward the other bone screw. As the spinal rod travels subcutaneously, the surgeon is free to move the spinal rod along, away from, toward, and around the outer surface of the elongate member as needed to maneuver the distal end of the spinal rod around the tissues and boney structures adjacent the vertebral bones. The distal end of the spinal rod may be brought into contact with an outer surface of the other elongate member to provide a tactile indication that the distal end has reached the other pedicle screw assembly. Further, a proximal end of the spinal rod may be brought into contact with the outer surface of the adjacent elongate member to provide a tactile indication that the proximal end of the spinal rod is positioned above the associated pedicle screw assembly. The spinal rod may be lowered along the outer surfaces of the elongate members until the distal end engages the seat of one of the coupling devices and the proximal end engages the seat of the other coupling device. Next, a locking cap is slid over and along the outer surface of each elongate member and engaged with a lower end of the elongate member to fix the spinal rod to the coupling device. An upper end of each of the elongate members may then be broken off or released, then removed before the working channels are closed.

In accordance with another aspect, a method of using a spinal fixation system is also provided wherein the spinal fixation system comprises a bone screw, a spinal rod, and a coupling device for connecting the spinal rod to the bone screw. The spinal fixation system provides multi-step locking of a spinal rod to a bone screw including an initial configuration for installing the bone screw, an intermediate fixation configuration for loosely connecting the spinal rod to the bone screw, and a final locking configuration where the spinal rod is fixed to the bone screw. In the initial configuration, the coupling device is pivotally and rotatably connected to the bone screw such that the connected coupling device and bone screw may be passed through a working channel and secured to a bone. The spinal rod is advanced through the working channel and positioned on a seat of the coupling device before a locking cap is slid downward along an elongate member of the coupling device. The locking cap is engaged with a lower portion of the elongate member to loosely capture the spinal rod on the seat of the coupling device. Next, the elongate member is manipulated to shift the spinal fixation system to the intermediate fixation configuration and rigidly fix the connection between the coupling device and the bone screw. In an alternative approach, the elongate member is manipulated to shift the spinal fixation system to the intermediate fixation configuration before the spinal rod is positioned on the seat and the locking cap is used to capture the spinal rod on the seat. With the spinal fixation system in the intermediate fixation configuration, the coupling device is fixed relative to the bone screw while the locking cap permits the spinal rod to be slidably repositioned on the seat. The locking cap is then manipulated to shift the spinal fixation system to a final locking configuration and clamp the spinal rod against the seat of the coupling device. At this point, the spinal rod, coupling device, and pedicle screw are rigidly fixed relative to each other.

BRIEF DESCRIPTION OF THE DRAWINGS

FIG. 3A is a side elevational view of a pair of pedicle screw subassemblies including a bone screw and a guide member similar to the components of the pedicle screw assembly of FIG. 1, with FIG. 3A showing the pedicle screw subassemblies being connected to respective vertebral bones beneath a patient's skin using driver sleeves;

FIGS. 4-6 are a series of side elevational views of the pedicle screw subassemblies of FIG. 3A illustrating an exemplary procedure for securing a spinal rod to the pedicle screw subassemblies;

FIG. 15 is a perspective view of a spinal fixation system in accordance with another form of the present invention showing a spinal rod held by a pedicle screw assembly by a locking cap;

FIG. 16 is a perspective view of a lower capture portion of the locking cap of FIG. 15;

DETAILED DESCRIPTION OF THE PREFERRED EMBODIMENTS

Figure 1:
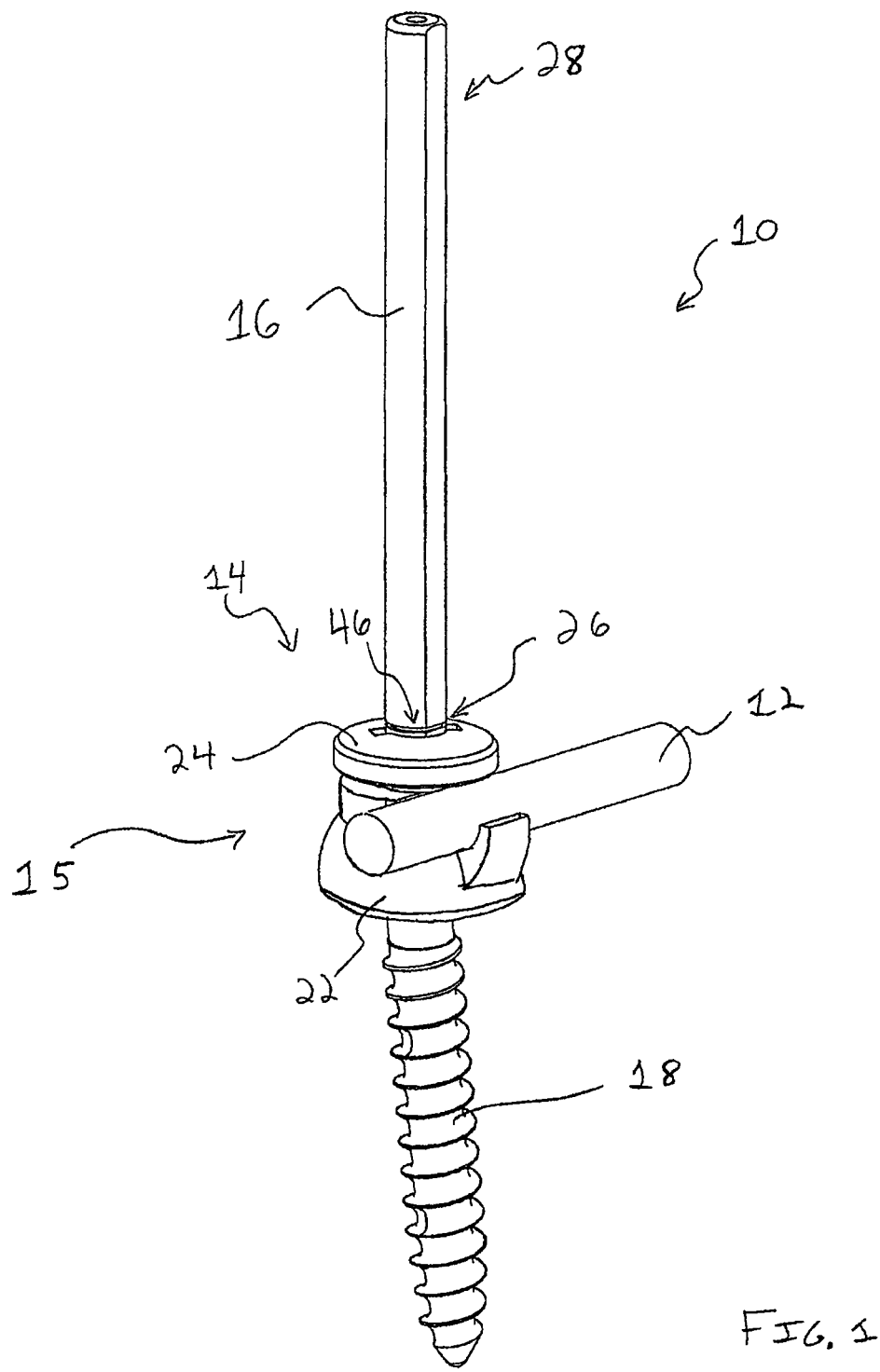
FIG. 1 is a perspective view of a spinal fixation system in accordance with the present invention showing a spinal rod held by a pedicle screw assembly.

In FIG. 1, a spinal fixation system 10 in accordance with one form of the present invention is depicted. The spinal fixation system 10 comprises a fixation element, such as a spinal rod 12, and a pedicle screw assembly 14 for securing the spinal rod 12 to a vertebra. The pedicle screw assembly 14 comprises a coupling device 15 and a bone screw 18. The coupling device 15 is operable to secure the spinal rod 12 relative to the bone screw 18. The coupling device 15 has an elongate member, such as guide member 16, for guiding the spinal rod 12 onto an open seat of the coupling device 15, such as a saddle body 22. With the spinal rod 12 received on the saddle body 22, a lock device, such as a locking cap 24, is fit onto and guided down along the guide member 16 and engaged with threads 46 of the guide member 16 to fix the spinal rod 12 against the saddle body 22.

Figure 2A:
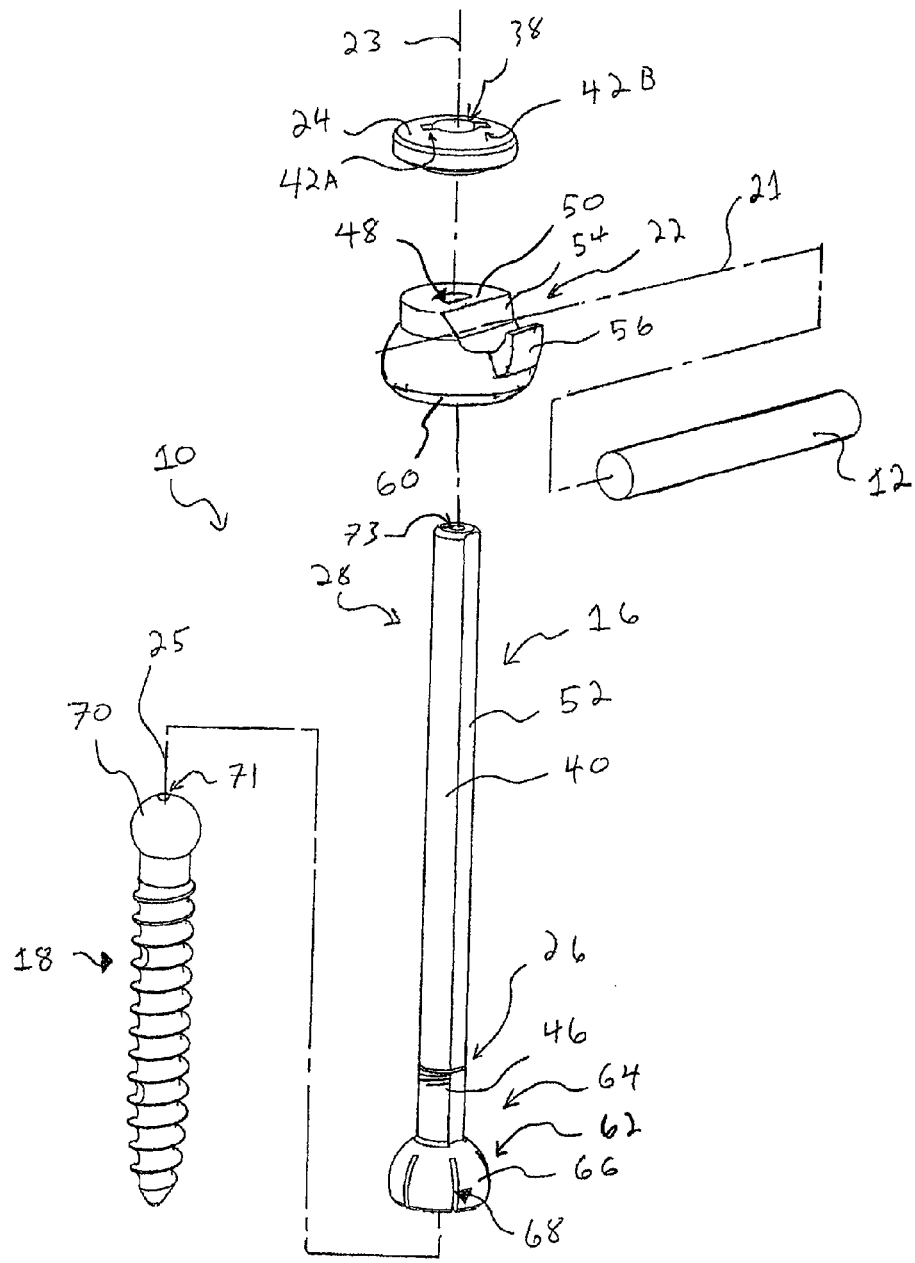
FIG. 2A is an exploded perspective view of the spinal fixation system of FIG. 1 showing a locking cap and a saddle body that travel along a guide member and a socket of the guide member that connects to a head of a bone screw.

As can be seen in FIGS. 1 and 2A, the spinal rod 12 rests upon a seating surface 54 of the saddle body 22 generally along an axis 21 that is laterally offset from an axis 23 of the guide member 16. The spinal rod 12 may be slid along and maneuvered around the guide member 16 with any contact between the spinal rod 12 and the guide member 16 providing tactile feedback regarding the position of the spinal rod 12 relative to the saddle body 22. Further, the lateral spacing between the axis 21 and the axis 23 allows the spinal rod 12 to be lowered downwardly along the guide member 16 into position on the saddle body 22 without having to fit the spinal rod 12 through slots or other alignment structures of the pedicle screw assembly 14. In this manner, the spinal rod 12 may be maneuvered around boney structures and tissues adjacent the pedicle screw assembly 14. Once the locking cap 24 has fixed the spinal rod 12 within the saddle body 22, a counter-torque may be applied to the guide member 16 to fracture the guide member 16 at a break-off section 26 so that an upper projection portion 28 of the guide member 16 can be removed.

In one approach, a pair of pedicle screw assemblies 14 are attached to respective vertebral bones via a small incision adjacent each vertebral bone. The spinal rod 12 may be inserted through one of the incisions and passed subcutaneously between the pedicle screw assemblies 14 so as to orient the rod 12 to span the saddle bodies 22 of the pedicle screw assemblies 14. The guide member 16 of each pedicle screw assembly 14 acts as a guidepost for directing movement of the spinal rod 12, with contact between the spinal rod 12 and the guide member 16 indicating that the spinal rod 12 is positioned above the saddle body 22 of the respective pedicle screw assembly 14. Although the guide members 16 partially restrict lateral movement of the spinal rod 12, e.g., the guide members 16A, 16B of FIG. 4 restrict movement of a spinal rod 82 into the page along the Z-axis, the surgeon is able to maneuver the spinal rod 12 using substantially unencumbered movement out of the page along the Z-axis, forward/backward along the X-axis, upward/downward along the Y-axis, and rotationally around the X-, Y-, and Z-axes.

Figure 2B:
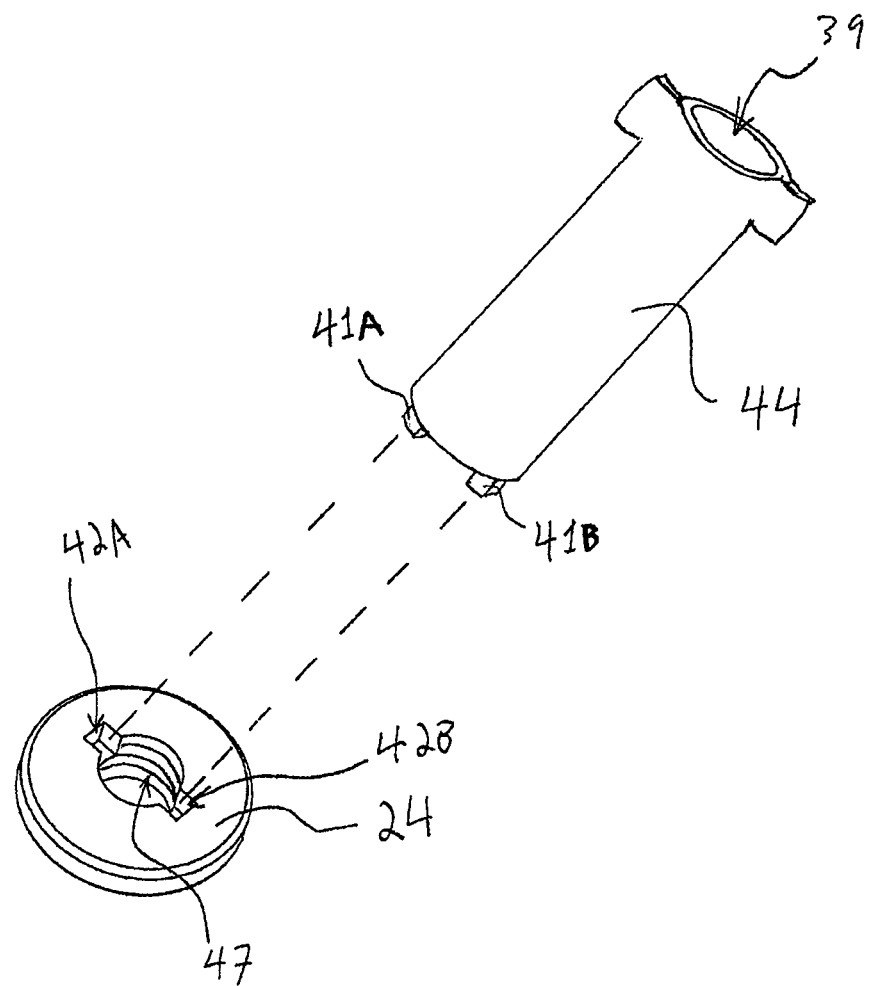
FIG. 2B is an exploded perspective view of the locking cap of FIG. 2A and a rod locking sleeve for manipulating the locking cap, FIG. 2B showing an engagement interface between the rod locking sleeve and the locking cap.

Returning to FIG. 2A, the locking cap 24 has a central throughopening 38 sized to receive shaft 40 of the guide member 16. The locking cap 24 also has tool receiving slot cutouts 42A, 42B extending radially from diametrically opposed sides of the opening 38 for engaging a tool, such as a rod locking sleeve 44, as shown in FIG. 2B. The rod locking sleeve 44 has an opening 39 for receiving the guide member shaft 40 therethrough and prongs 41A, 41B for engaging the cutouts 42A, 42B on the locking cap 24. In alternative embodiments, the prongs 41A, 41B could be replaced by any number of drive interfaces, such as a hex drive, with the locking cap 24 being similarly adapted.

In some instances, the spinal rod 12 may sit proud of the saddle body 22 due to tissues surrounding the pedicle screw 14. To reduce the spinal rod 12 into position on the saddle body 22, the surgeon may use the locking cap 24 and the rod locking sleeve 44 to apply a force to the spinal rod 12 to urge and shift the rod 12 toward the saddle body 22. More specifically, the prongs 41A, 41B are engaged within the cutouts 42A, 42B to releasably connect the rod locking sleeve 44 to the locking cap 24, as shown in FIG. 2B. Next, the connected locking cap 24 and rod locking sleeve 44 are fit onto and moved along the shaft 40 of the guide member 16 until the locking cap 24 contacts the spinal rod 12. Applying downward forces to the rod locking sleeve 44 moves the locking cap 24 and the spinal rod 12 downward until the locking cap 24 reaches the threads 46 of the guide member 16 (see FIG. 2A). The rod locking sleeve 44 is rotated to threadingly engage internal threads 47 of the locking cap 24 with the threads 46 of the guide member 16 and clamp the spinal rod 12 against the saddle body 22. In an alternative configuration, the locking cap 24 may connect to the guide member 16 using a bayonet-style lock or other approach. The rod locking sleeve 44 can be used to impart rotation and/or axial movement to the locking cap 24 in these alternative configurations as well.

The saddle body 22 has a throughbore 48 sized to receive the shaft 40 of the guide member 16, as shown in FIG. 2A. The throughbore 48 and guide member 16 can have a non-rotational mating fit so that the cross-sectional configuration of each is the same and is non-circular. As illustrated, the throughbore 48 and guide member 16 each have a D-shaped cross-sectional configuration with flats 50 and 52, respectively, which are in confronting relation with the shaft 40 extending in the throughbore 48.

With continued reference to FIG. 2A, a seating surface 54 extends along an arm portion 56 of the saddle body 22 and partially around the spinal rod 12. In an alternative configuration, the saddle body 22 comprises a substantially planar surface for receiving the spinal rod 12 that does not extend around the spinal rod 12. The saddle body 22 also has a cup portion 60 that is operable to constrict a flexible socket 62 of the guide member 16 about a head 70 of the bone screw 18 as the saddle body 22 moves axially downward toward a lower end 64 of the guide member 16 and over the flexible socket 62. The flexible socket 62 comprises a plurality of fingers 66 separated by longitudinal slits 68 that resiliently deform according to the axial position of the cup portion 60 on the flexible socket 62. More specifically, when the saddle body 22 is not fully seated on the flexible socket 62, the cup portion 60 constricts the fingers 66 of the flexible socket 62 about the bone screw head 70 but permits relative movement between the flexible socket 62 and the head 70. The engagement between the flexible socket 62 and the bone screw head 70 forms a ball-and-socket connection that permits the guide member 16 to pivot and rotate relative to the bone screw 18. Preferably, there is sufficient friction between the flexible socket 62 and the bone screw head 70 to hold the flexible socket 62 on the head 70 at a set position when the guide member 16 is released. To fix the flexible socket 62 about the bone screw head 70, the locking cap 24 is tightened to shift the cup portion 60 of the saddle body 22 farther axially downward and further constrict the plurality of fingers 66 about the bone screw head 70. The threaded engagement between the locking cap 24 and the threads 46 of the guide member 16 keeps the locking cap 24 in an axial position desired to maintain the fixed relation between the guide member 16 and the bone screw 18, and the respective axes 23 and 25 thereof.

A method of using the spinal fixation system 10 in a minimally invasive surgical approach is illustrated in FIGS. 3A-6. The method utilizes a pair of pedicle screw assemblies 14A, 14B and the components of the assemblies will be identified using reference numbers that are identical to the corresponding components discussed above with a letter A or B added to designate the respective pedicle screw assembly 14A or 14B. Initially, a small incision is made in a patient's skin and other tissues 79 adjacent a first vertebral bone, such as pedicle 80A, and an optional guide wire (not shown) is brought into contact with the first pedicle 80A. If so desired, serial dilators (not shown) are passed over the guide wire and into contact with the first pedicle 80A before an outer sleeve (not shown) is passed over the dilators and secured to the pedicle 80A to form a working channel 81. The outer sleeve may have a non-circular profile in order to accommodate portions of the pedicle screw assembly 14, such as the arm portion 56 of the saddle body 22. The outer sleeve may also have a slot extending along the length of the outer sleeve to pass the spinal rod 82 therethrough. This procedure is repeated for a second level vertebral bone, such as pedicle 80B, to form a working channel 83. The serial dilators and the guide wire may then be removed before drilling and tapping of the pedicle.

Figure 3B:
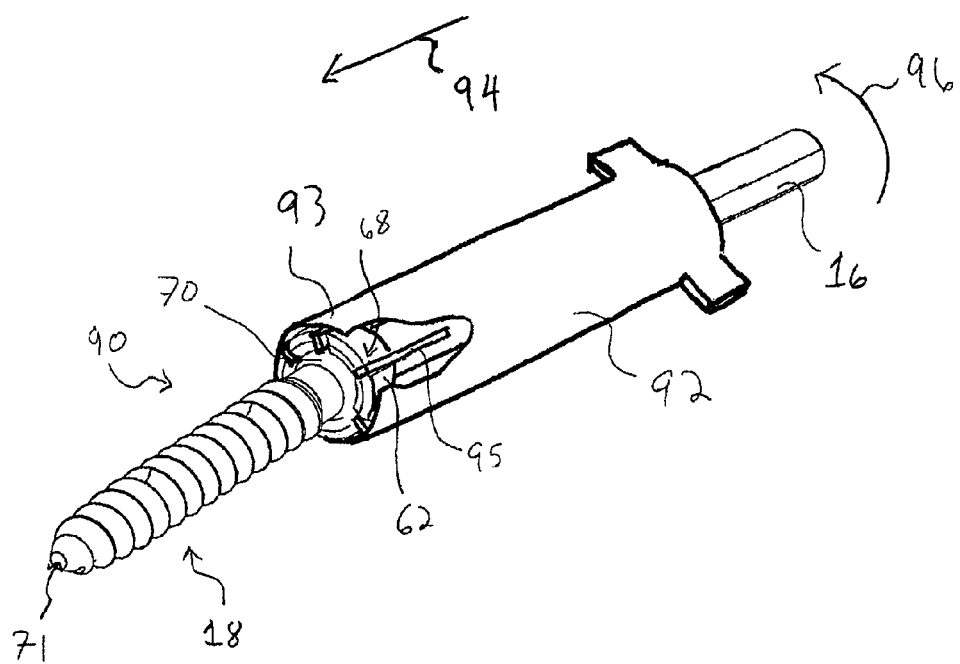
FIG. 3B is a perspective view of a pedicle screw subassembly and the driver sleeve of FIG. 3A having a portion of the driver sleeve removed to show internal longitudinal fins of the driver sleeve.

Pedicle screw subassemblies 90A, 90B are formed by connecting the flexible socket 62A, 62B of the guide member 16A, 16B to the respective bone screw head 70A, 70B. The pedicle screw subassemblies 90A, 90B may be preassembled or may be assembled during a surgical procedure. Driver tools, such as driver sleeves 92A, 92B, are used to rigidly fix the flexible sockets 62A, 62B on the respective bone screw heads 70A, 70B and drive the subassemblies 90A, 90B into the pedicles 80A, 80B. As shown in FIG. 3B, once the driver sleeve 92 has been moved downwardly over the flexible socket 62 of the guide member 18 in direction 94, a rim 93 of the sleeve 92 is sized to collapse the flexible socket 62 about the bone screw head 70 and fixedly hold the subassembly 90 together. In the illustrated embodiment, the bone screw 18 has a cannula 71 (see FIG. 2A) that may be aligned with a cannula 73 of the guide member 16 and permit the subassembly 90 to be passed along a guide wire (not shown) and into contact with a vertebral bone.

As shown in FIG. 3B, the driver sleeve 92 has a plurality of internal longitudinal fins 95 that extend into the longitudinal slits 68 of the flexible socket 62. The engagement between the internal longitudinal fins 95 of the driver sleeve 92 and the longitudinal slits 68 of the flexible socket 62 permits rotation of the driver sleeve 92 in rotary direction 96 to rotate the subassembly 90. This movement is also shown in FIG. 3A, where rotation of the driver sleeves 92A, 92B in rotary directions 96A, 96B produces concurrent rotation of the pedicle screw subassemblies 90A, 90B and driving of the bone screws 18A, 18B into the respective pedicles 80A, 80B. In an alternative embodiment (not shown), the bone screw head 70 has longitudinal slits aligned with the longitudinal slits 68 of the flexible socket 62 and the internal longitudinal fins 95 of the driver sleeve 92 are sized to engage the slits on the bone screw head 70 as well as the longitudinal slits 68 of the flexible socket 62.

With the pedicle screw subassemblies 90A, 90B secured to the pedicles 80A, 80B, the driver sleeves 92A, 92B are removed and the saddle bodies 22A, 22B are slid downwardly along the guide member shafts 40A, 40B, as shown in FIG. 4A. The saddle bodies 22A, 22B are slid in directions 98A, 98B to seat the cup portions 60A, 60B of the saddle bodies 22A, 22B on the flexible sockets 62A, 62B and to partially constrict the flexible sockets 62A, 62B about the bone screw heads 70A, 70B. The guide members 16A, 16B preferably have sufficient length to extend outward from the respective working channels 81, 83 above the tissue 79 of the patient. In this manner, a surgeon may visually align the spinal rod 82 on one side of the guide members 16A, 16B above the patient's skin before inserting the spinal rod 82 into the working channel 81 adjacent the first pedicle 80A. The guide members 16A, 16B may also have upper threads 100A, 100B for temporarily holding the locking caps 24A, 24B above the saddle bodies 22A, 22B.

Figure 4:
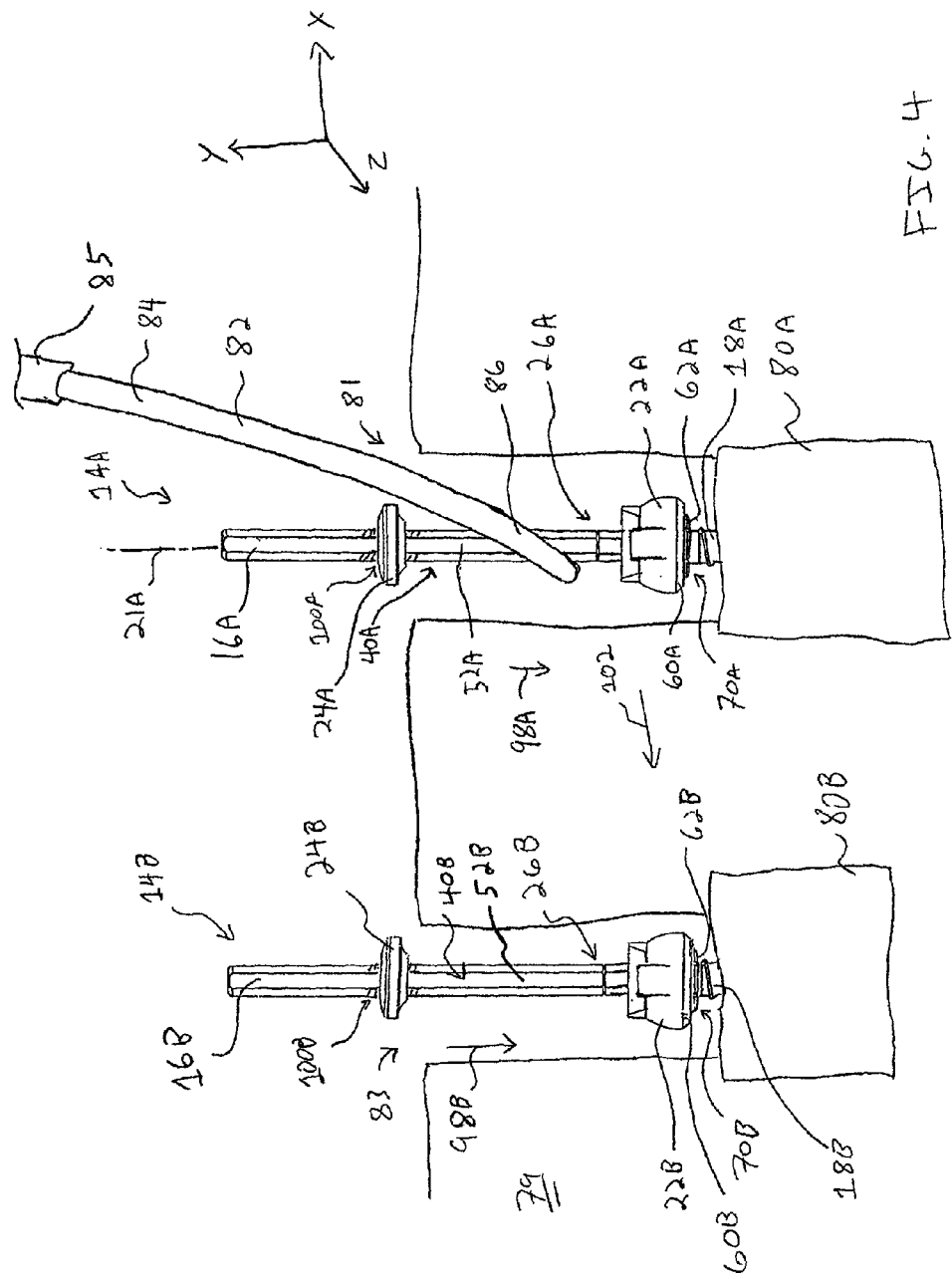
Figure 7:
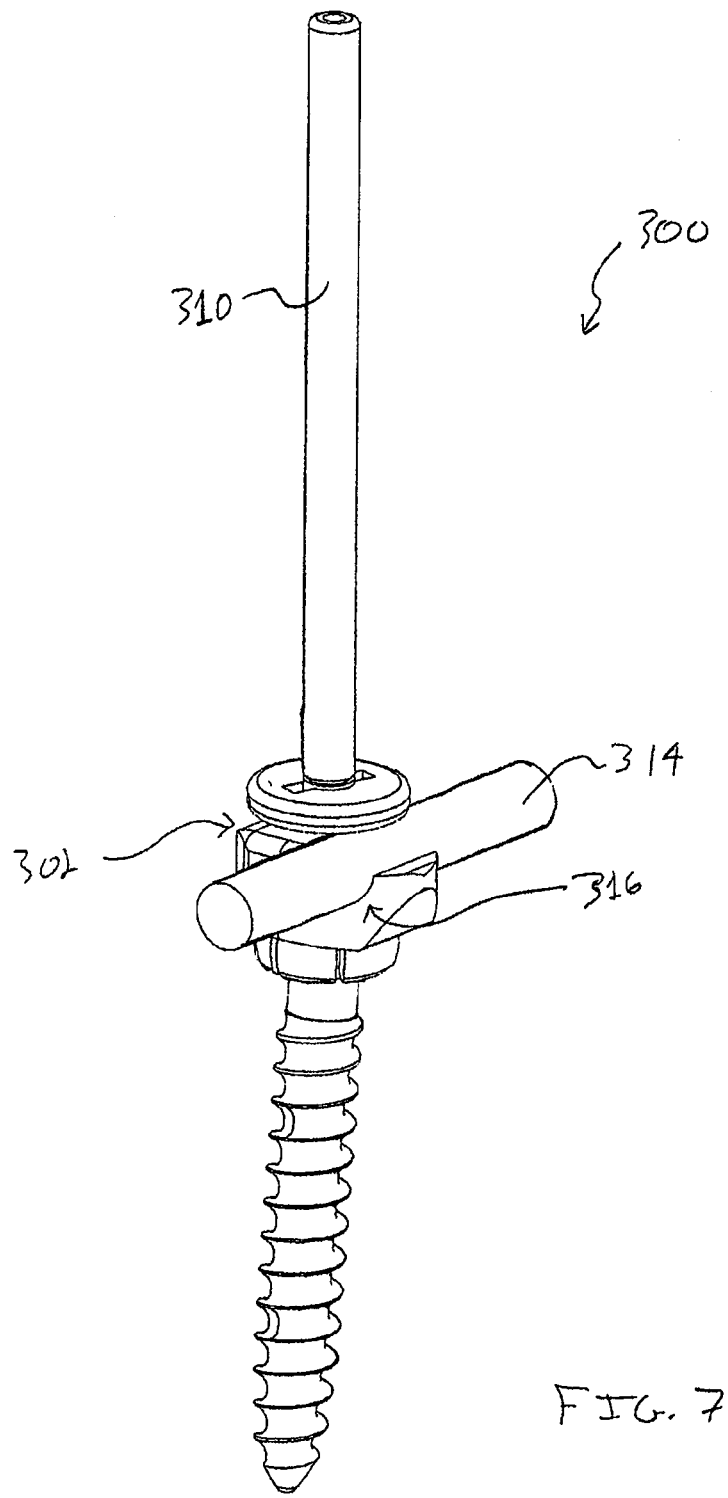
FIG. 7 is a perspective view of a spinal fixation system in accordance with another form of the present invention showing a spinal rod held by a pedicle screw assembly.

A rod inserter 85 is used to guide a distal end 86 of the spinal rod 82 through the working channel 81 adjacent the pedicle 80A at a transverse angle relative to the guide member axis 21A, downward toward the saddle body 22A, beneath tissue 79, and over toward the saddle body 22B in direction 102, as shown in FIG. 4. One rod inserter 85 that may be used to insert the spinal rod 82 is disclosed in U.S. Patent Application Publication No. 2008/0039839 to Songer et al., which published on Feb. 14, 2008, the entirety of which is hereby incorporated by reference. Although the spinal rod 82 will be moving subcutaneously between the two working channels 81, 83, the surgeon can guide the spinal rod 82 into contact with the flats 52A, 52B of the guide members 16A, 16B and receive tactile feedback that the distal end 86 of the spinal rod 82 is disposed above the saddle body 22A and a trailing end 84 of the spinal rod 82 is disposed above the saddle body 22B. Once the spinal rod 82 is properly oriented, the spinal rod 82 is lowered onto the saddle bodies 22A, 22B using the guide member shafts 40A, 40B as guides. The spinal rod 82 slides along flats 52A, 52B of the guide members 16A, 16B such that the contact between flats 52A, 52B and the spinal rod 82 provides a smooth sliding interface therebetween. In the preferred embodiment, the spinal rod 82 has a round cross-section for producing a line contact with the flats 52A, 52B, although other cross-sectional configurations may be used. In another approach, the spinal rod 82 may be inserted generally parallel to the guide member axis 21A into the working channel 81 before the distal end 86 of the spinal rod 82 is directed toward the saddle body 22B. Further, the spinal rod 82 may be inserted through a third incision (not shown) into the tissue 79 and along a path transverse to the guide member 16A.

Once the spinal rod 82 is seated in the saddle bodies 22A, 22B, the locking caps 24A, 24B can be disengaged from the threads 100A, 100B, slid downwardly in directions 98A, 98B along the shafts 40A, 40B, and tightened onto the respective guide member threads 46 to fix the spinal rod 82 within the saddle bodies 22A, 22B. Turning to FIG. 5A, a pair of rod locking sleeves 44A, 44B are operable to disengage the locking caps 24A, 24B from the threads 100A, 100B, translate the locking caps 24A, 24B downward in directions 110A, 110B, and to rotate the locking caps 24A, 24B in directions 112A, 112B, as discussed above with respect to FIG. 2B. This locks the locking caps 24A, 24B onto the spinal rod 82 and clamps the spinal rod 82 against the saddle bodies 22A, 22B.

Once the spinal rod 82 has been clamped against the saddle bodies 22A, 22B, the rod locking sleeves 44A, 44B may be used to stabilize the pedicle screw assemblies 14A, 14B while a tool 45 is used to break off the upper projection portions 28A, 28B, as shown in FIG. 5B. The tool 45 comprises a socket 49 having a non-rotational mating fit with the upper projection portions 28A, 28B of the guide members 16A, 16B. For example, the socket 49 may have a D-shaped cross-sectional configuration with a flat adapted to be in confronting relation with flats 52A, 52B. To break off the upper projection portions 28A, 28B, the socket 49 is slid downward onto the upper projection portion 28A and a T-handle 51A of the rod locking sleeve 44A is grasped or otherwise secured. Next, a handle 53 of the tool 45 is grasped and rotated in direction 55 to apply a torque to the upper projection portion 28A while the T-handle 51A is held stationary. The combination of the torque from the rotating tool 45 and the counter torque from the T-handle 51A causes the upper projection portion 28A to shear off at the break-off section 26A (see FIG. 4). The upper projection portion 28A is removed and the tool 45 is used to break off upper projection portion 28B of the guide member 16B in a similar manner. In a preferred approach, the torque used to break off the upper projection portions 28A, 28B is slightly greater than the torque used to lock the locking caps 24A, 24B.

After the upper projection portions 28A, 28B have been broken off and removed, the rod locking sleeves 44A, 44B are removed from the working channels 81, 83. Outer sleeves and/or other tools used to retract the tissue 79 are removed and the incisions are closed, as shown in FIG. 6. At this point, the pedicle screw subassemblies 14A, 14B, the pedicles 80A, 80B, and the spinal rod 82 are in fixed relation to one another. Although the remaining portions of the guide members 16A, 16B are illustrated extending above the locking caps 24A, 24B, the break-off sections 26A, 26B may be positioned along the guide members 26A, 26B such that the remaining portions of the guide members 16A, 16B do not extend above the caps 24A, 24B.

Figure 8:
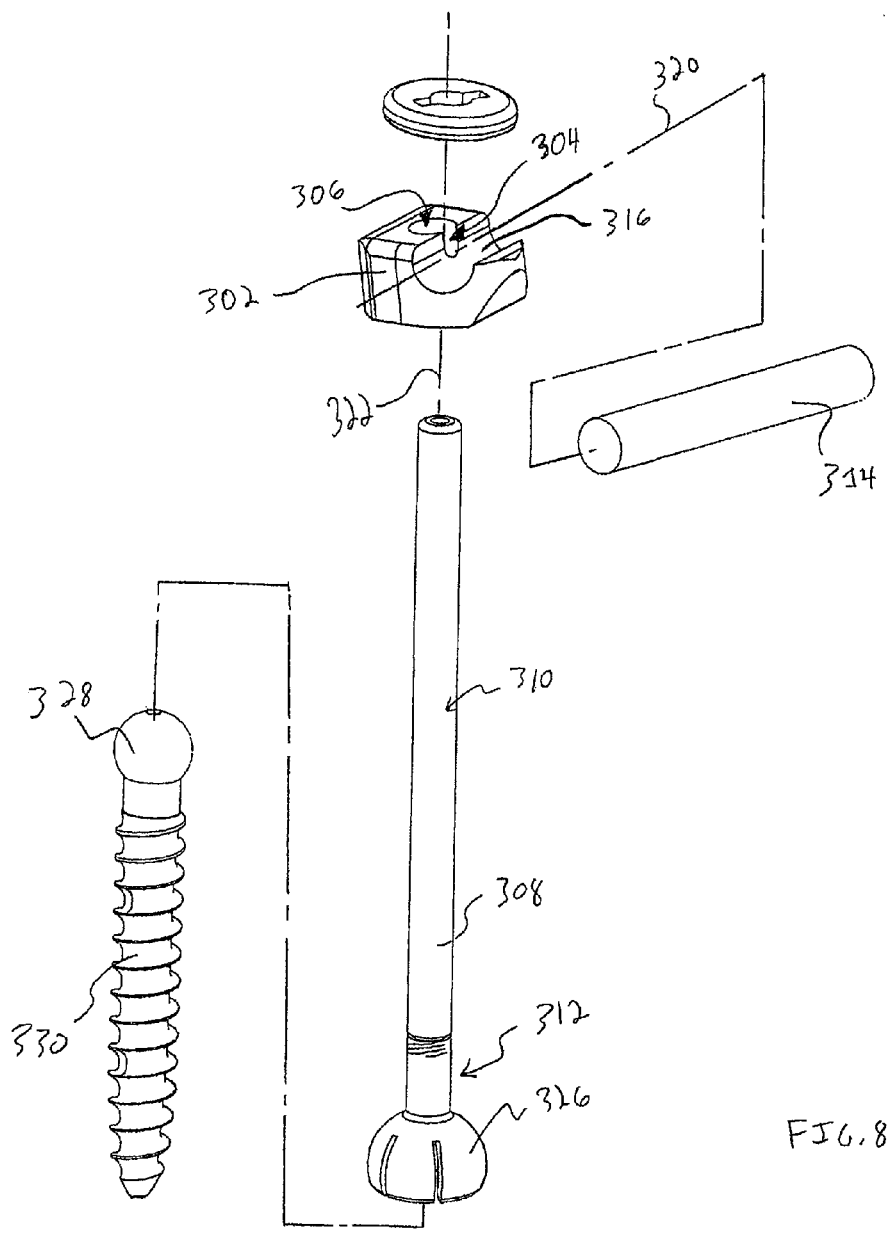
FIG. 8 is an exploded perspective view of the spinal fixation system of FIG. 7 showing a locking cap and a saddle body that travel along a guide member and a socket of the guide member that connects to a head of a bone screw.
Figure 9:
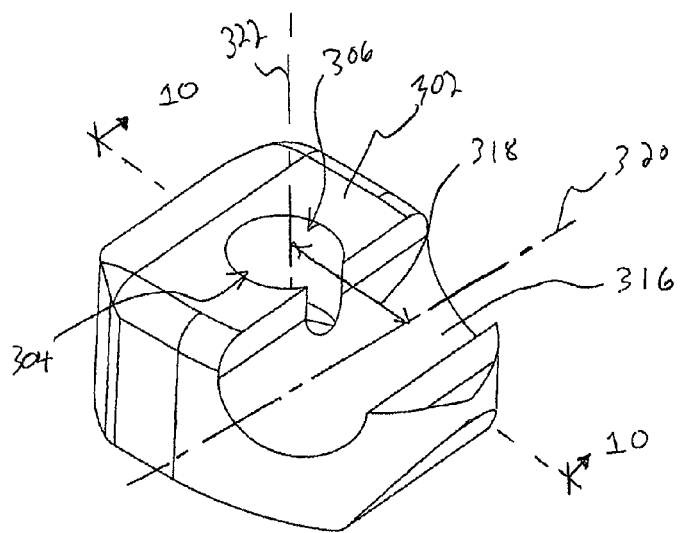
FIG. 9 is a perspective view of the saddle body of FIG. 8 showing an open seating surface of the saddle body.
Figure 10:
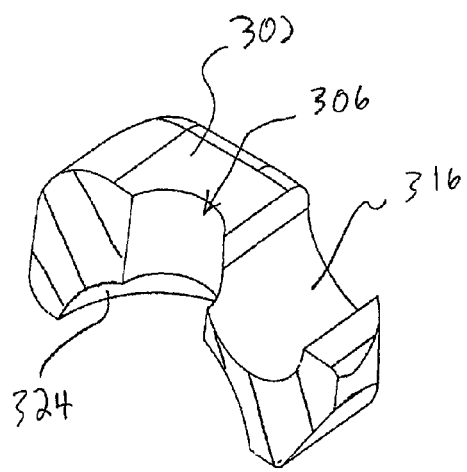
FIG. 10 is a cross-sectional view taken across line 10-10 in FIG. 9 that shows a throughbore of the saddle body opening into an engagement cup.

A spinal fixation system 300 in accordance with another form of the present invention is illustrated in FIGS. 7-10. The spinal fixation system 300 is similar to the spinal fixation system 10 shown in FIGS. 1-6 but, unlike the spinal fixation system 10, the spinal fixation system 300 has a saddle body 302 with a cutout 304 in communication with a throughbore 306 for receiving a shaft 308 of a guide member 310, as shown in FIG. 8. The cutout 304 allows a distal portion 312 of the guide member 310 to abut a spinal rod 314 when the spinal rod 314 is received against a seating surface 316 of the saddle body 302. This abutting relation permits a distance 318 between an axis 320 of the spinal rod 314 and an axis 322 of the guide member 310 to be minimized, as shown in FIG. 9. Because of the proximity between the spinal rod 314 and the guide member 310 within the saddle body 302, a surgeon may slide the spinal rod 314 downward along the guide member shaft 308 and onto the seating surface 316 in one fluid movement without any lateral movement of the spinal rod 314 away from the guide member shaft 310. Further, the throughbore 306 opens into an engagement cup 324 (see FIG. 10) for constricting a flexible socket 326 of the guide member 310 about a spherical head 328 of a bone screw 330, as shown in FIG. 8. The engagement cup 324 is similar to the cup portion 60 of the saddle body 22 discussed above. In an alternative embodiments, the bone screw head 328 may have a non-spherical shape, such as cylindrical or elliptical, to provide a desired range of motion of the guide member 310 relative to the bone screw 330.

Figure 11:
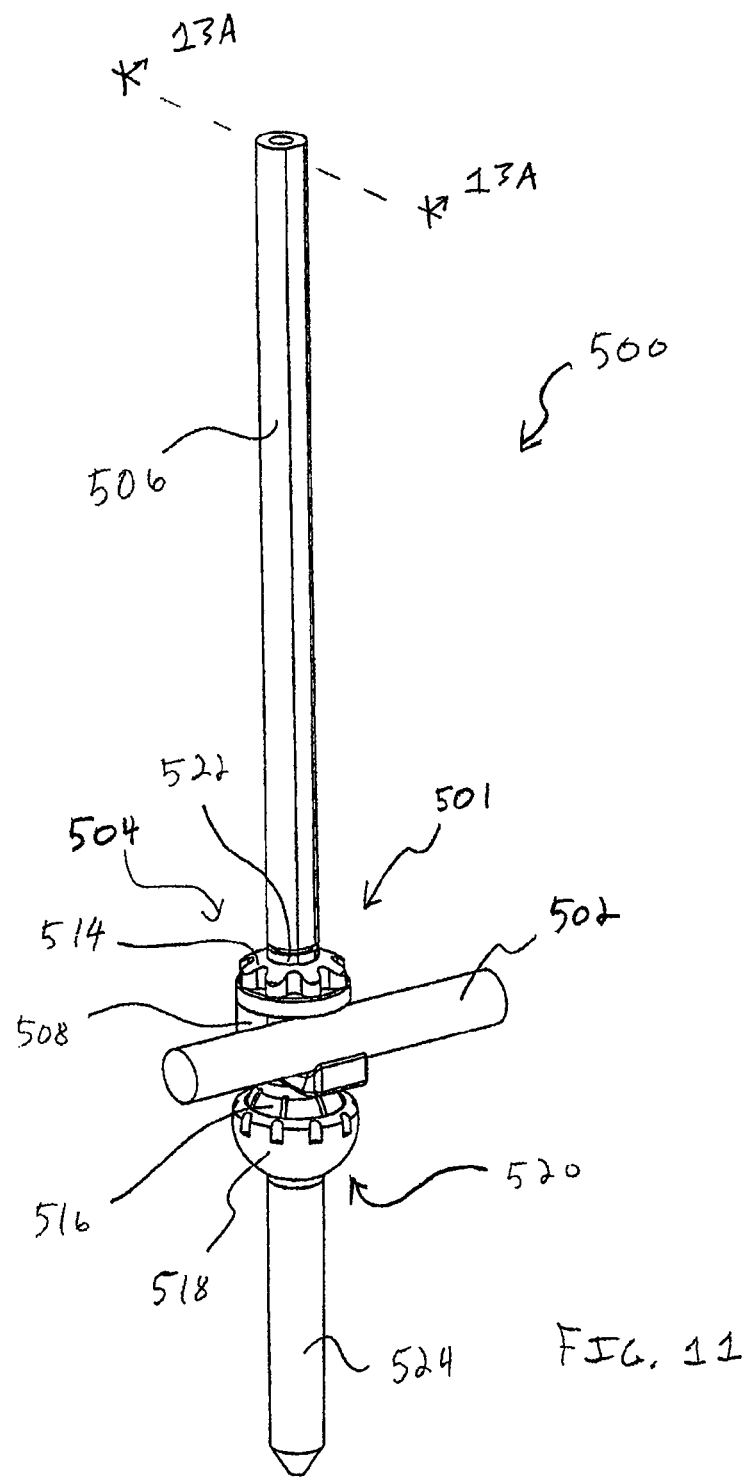
FIG. 11 is a perspective view of a spinal fixation system in accordance with another form of the present invention showing a spinal rod held within a pedicle screw assembly.

A spinal fixation system 500 in accordance with another form of the present invention is shown in FIGS. 11-14. The spinal fixation system 500 has a ball-and-socket connection between a coupling device 501 and a bone screw 520. The coupling device 501 has an open seat, such as a pivot body 508, with a flexible ball 516 that expands within a bone screw head 518, rather than a guide member flexible socket 62, 326 that collapses about a spherical bone screw head 70, 328, as in the spinal fixation systems 10, 300 discussed above. The spinal fixation system 500 comprises a spinal rod 502 and a pedicle screw assembly 504 for securing the spinal rod 502 to a vertebra, as shown in FIG. 11. A locking cap 514 is passed over and along a guide member 506 upstanding from the pivot body 508 until internal threads 568 (see FIG. 13A) of the locking cap 514 engage threads 570 on a lower portion 522 of the guide member 506. Returning to FIG. 11, tightening the locking cap 514 onto the guide member threads 570 causes the flexible ball 516 to expand within the bone screw head 518 and fix the pivot body 508 at a desired angle relative to a shank 524 of the bone screw 520, as will be discussed in greater detail below.

Figure 12:
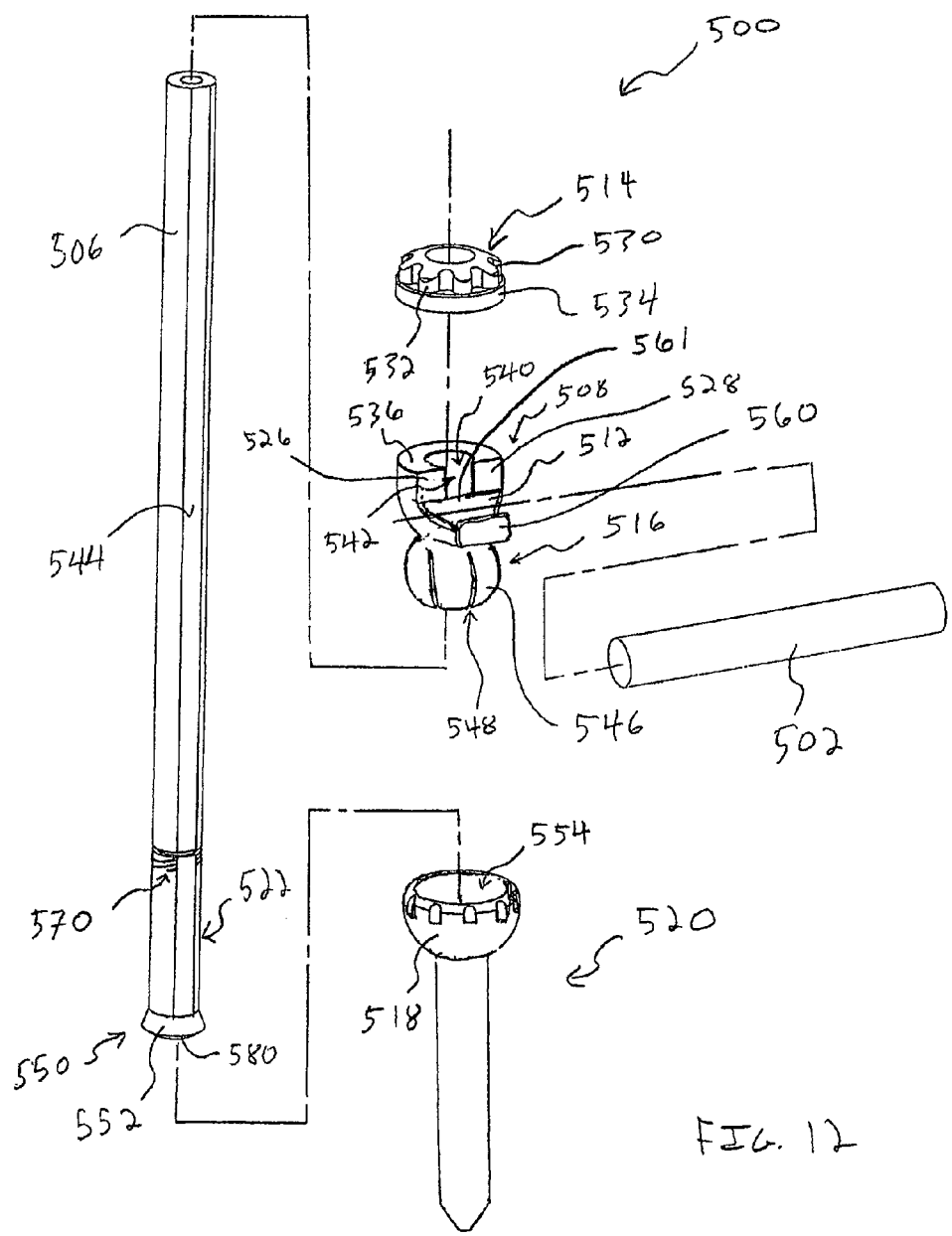
FIG. 12 is an exploded perspective view of the spinal fixation system of FIG. 11 showing a locking cap and a pivot body that travel along a guide member and a distal end of the guide member that is disposed within the pivot body.

With reference to FIG. 12, the locking cap 514 has an upper portion 530 with a plurality of teeth 532 for engaging a rod locking sleeve, e.g., a sleeve similar to the rod locking sleeve 44. A lower portion 534 of the locking cap 514 may rest against a seat 536 of the pivot body 508 after the locking cap 514 and the pivot body 508 have been passed over the guide member 506 and the locking cap 514 is threaded onto the threads 570 of the guide member 506. The pivot body 508 has a throughbore 540 and a cutout 542 in communication with the throughbore 540 such that a lower portion 522 of the guide member 506 abuts the spinal rod 502 when the spinal rod 502 rests upon a seating surface 512 of the pivot body 508, in a manner similar to the operation of cutout 304 discussed above with respect to the spinal fixation system 300. The guide member 506 may include a flat 544 that contacts the spinal rod 502 when the spinal rod 502 rests upon the seating surface 512. This contact, in combination with ends 526, 528 of the seat 536, holds the spinal rod 502 against an arm 560 of the pivot body 508. Further, a base 561 of the arm 560 abuts the flat 544 of the guide member 506 to resist rotation of the pivot body 508 about the guide member 506. With continued reference to FIG. 12, the ball 516 of the pivot body 508 comprises a plurality of fingers 546 separated by longitudinal slots 548. The plurality of fingers 546 cover a wedge 550 of the guide member 506 and a tapered annular surface 552 of the wedge 552 when the pivot body 508 is positioned over the distal portion 522 of the guide member 506.

The guide member 506 and the pivot body 508 are connected to the bone screw 520 by passing the ball 516, with the wedge 550 disposed therein, into the socket 554 of the bone screw 520. In one form, passing the ball 516 into a socket 554 comprises deflecting the plurality of fingers 546 inwardly against the guide member 506 to permit the ball 516 to pass into the socket 554. A rim 572 (see FIG. 13A) of the socket 554 may have an inner diameter that is smaller than a maximum outer diameter of the ball 516 such that the rim 572 retains the ball 516 on the wedge 550 and restricts movement of the ball 516 and wedge 550 outward from the socket 554. Alternative embodiments of the bone screw 520 are illustrated in FIGS. 13B and 13C. More specifically, bone screw 520A has a socket 554A with a rim 572A that is tilted relative to a longitudinal axis 571A of the bone screw 520A to provide an additional range of motion of the pivot body 508 in direction 573A from the longitudinal axis 571A, as shown in FIG. 13B. Preferably, the rim 572A has a higher portion 575A that compensates for a lower portion 569A and restricts movement of the ball 516 and the wedge 500 outward from the socket 554A. Another bone screw 520B is shown in FIG. 13C. The bone screw 520B has a socket 554B with a rim 572B, the rim 572B comprising a shallow pocket 577B to provide an increased range of motion of the pivot body 508 in the pocket 577B. The rim 572B has a raised sidewall 579B opposite the pocket 577B to compensate for the reduced engagement between the rim 572B and the pivot body 508 adjacent the pocket 577B. Like the rim 572A, the rim 572B restricts movement of the ball 516 and wedge 550 out of the socket 554B.

Figure 13A:
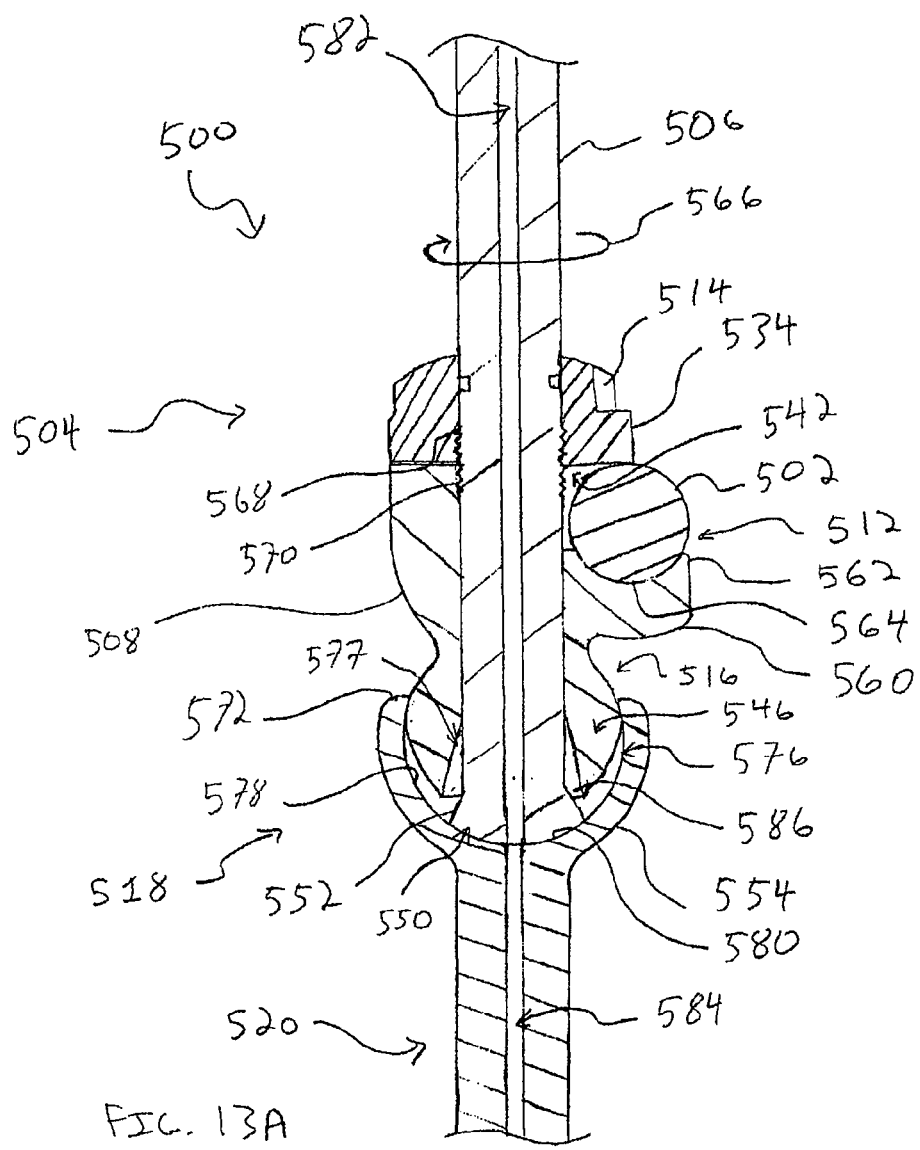
FIG. 13A is an enlarged, fragmented cross-sectional view of the spinal fixation system of FIG. 11 taken across line 13A-13A in FIG. 11 that shows the spinal rod received within the pedicle screw assembly before the locking cap is tightened to fix the spinal rod to the pedicle screw assembly.
Figures 13B, 13C:
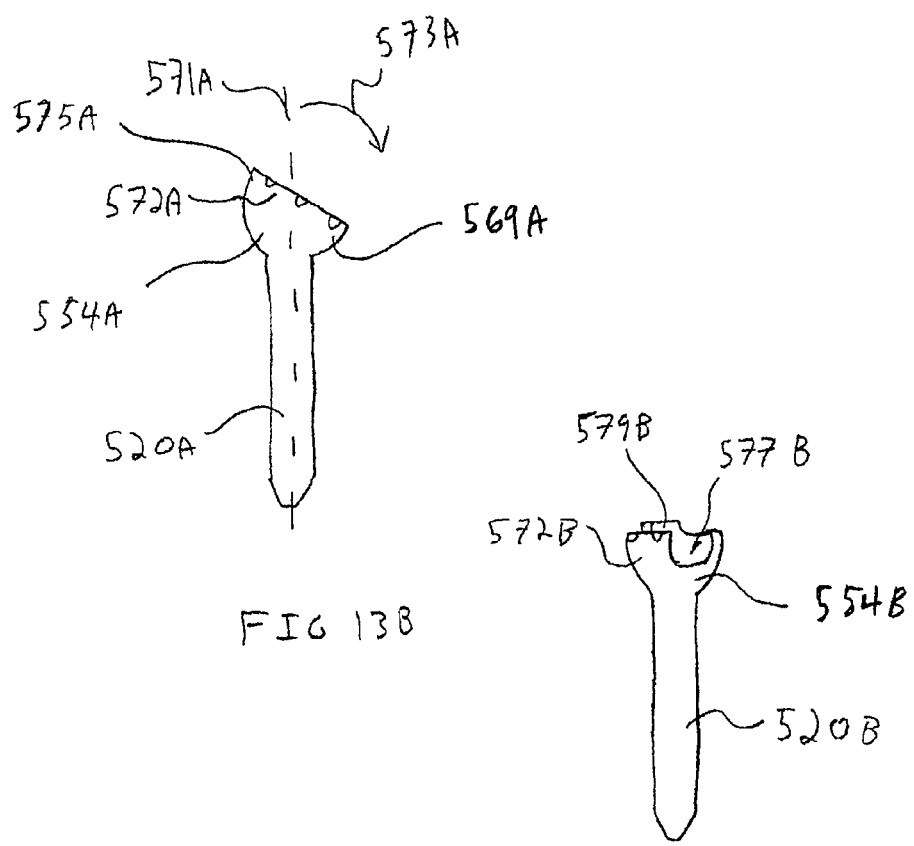
FIGS. 13B and 13C are side elevational views of alternative embodiments of a bone screw of the pedicle screw assembly of FIG. 11.
Figure 14:
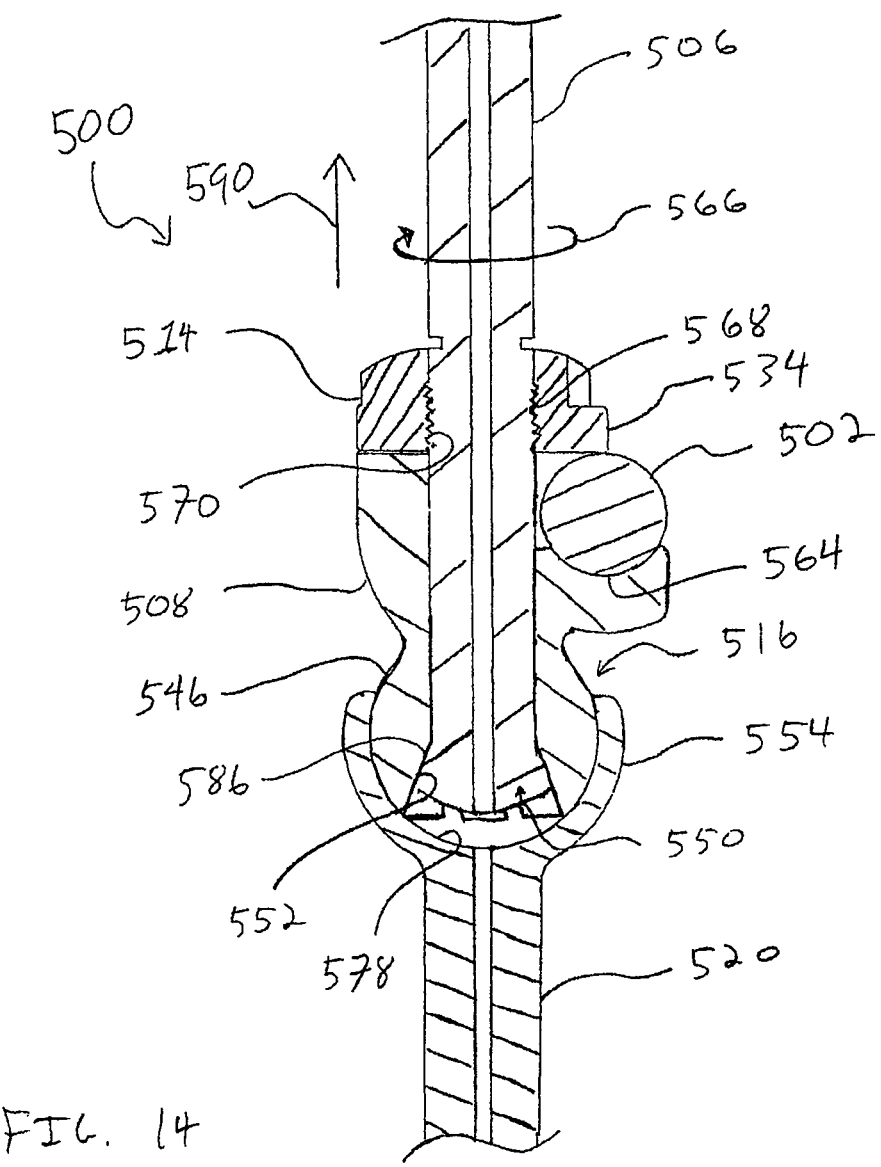
FIG. 14 is a cross-sectional view of the spinal fixation system of FIG. 11 that is similar to FIG. 13A and shows the pedicle screw assembly after the locking cap is tightened to fix the spinal rod within the pivot body.

With reference to FIGS. 13A and 14, a procedure for fixing the spinal rod 502 to the pedicle screw assembly 504 and fixing the orientation of the pivot body 508 relative to the bone screw 520 is shown. Initially, the spinal rod 502 is received on the seating surface 512 such that the arm 560 extends partially around the spinal rod 502 and a lip 562 restricts movement of the spinal rod 502 from the seating surface 512. In an alternative configuration, the arm 560 defines a generally planar surface or other configuration for receiving the spinal rod 502. The locking cap 514 is passed downward along the guide member 506 and rotated in direction 566 to engage the threads 568 of the locking cap 514 with the threads 570 of the guide member 506 which brings the locking cap 514 into an initial configuration where the lower portion 534 contacts the spinal rod 502. Bringing the locking cap 514 into the initial configuration restricts movement of the spinal rod 502 from the seating surface 512 and maintains the pivot body 508 at an axial position along the guide member 506.

As shown in FIG. 13A, there is initially a gap spacing 577 between an inclined surface 586 on the interior of each of the plurality of fingers 546 and the wedge 550 of the guide member 506 which permits the fingers 546 to deflect inwardly as the ball 516 is inserted into the socket 554. Further, a gap spacing 576 initially separates a portion of each of the plurality of fingers 546 from an engagement surface 578 of the socket 554 to permit the plurality of fingers 546 to expand radially outward against the socket 554, as will be discussed in greater detail below. Preferably, there is sufficient engagement between the plurality of fingers 546 and the socket 554 so that the pivot body 508 remains stationary when released. To provide smooth movement between the pivot body 508 and the bone screw 520, the wedge 550 may include a rounded tip 580 having a profile complimentary to the engagement surface 578 of the socket 554. In this manner, the guide member 506 may be pivoted and rotated relative to the bone screw 520 as needed to seat the spinal rod 502 on the pivot body 508. Further, the guide member 506 and the bone screw 520 may be aligned to permit passage of a guide wire through respective cannulas 582, 584 of the guide member 506 and bone screw 520.

As shown in FIG. 14, rotating the locking cap 514 in direction 566 to a locked configuration draws the guide member 506 upward in direction 590 relative to the pivot body 508. This movement brings the tapered annular surface 552 of the wedge 550 into contact with the inclined surfaces 586 of the plurality of fingers 546, which expands the fingers 546 radially outward and into engagement with the engagement surface 578 of the socket 554. The plurality of fingers 546 and/or the socket 554 may have a special surface finish, knurling, or coating to improve engagement between the fingers 546 and the socket 554. With the locking cap 514 in the locked configuration, the location of the wedge 550 within the flexible ball 516 is fixed, which keeps the plurality of fingers 546 in an outwardly expanded position and rigidly fixes the ball 516 within the socket 554. In this manner, the pivot body 508 is kept at a desired orientation relative to the bone screw 520. Rotating the locking cap 514 to the locked configuration also clamps the spinal rod 502 between the lower portion 534 of the locking cap 514 and the seating surface 512 of the pivot body 508, thereby fixing the spinal rod 502 within the pedicle screw assembly 504.

Figures 21, 22:
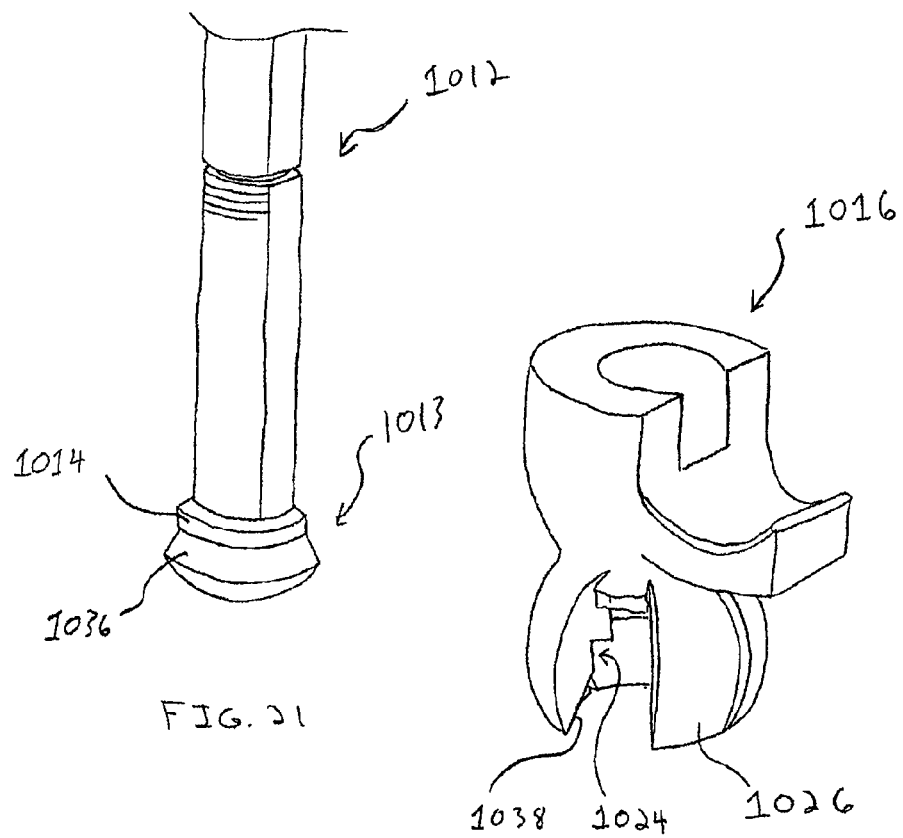
FIG. 21 is a perspective view of a guide member similar to the guide member of the spinal fixation system of FIG. 11, with FIG. 21 showing a step of the guide member.
FIG. 22 is a perspective view of a pivot body similar to the pivot body of the spinal fixation system of FIG. 11, with FIG. 22 showing a portion of the pivot body removed to show an interior recess that is complimentary to the step of the guide member of FIG. 21.
Figure 23:
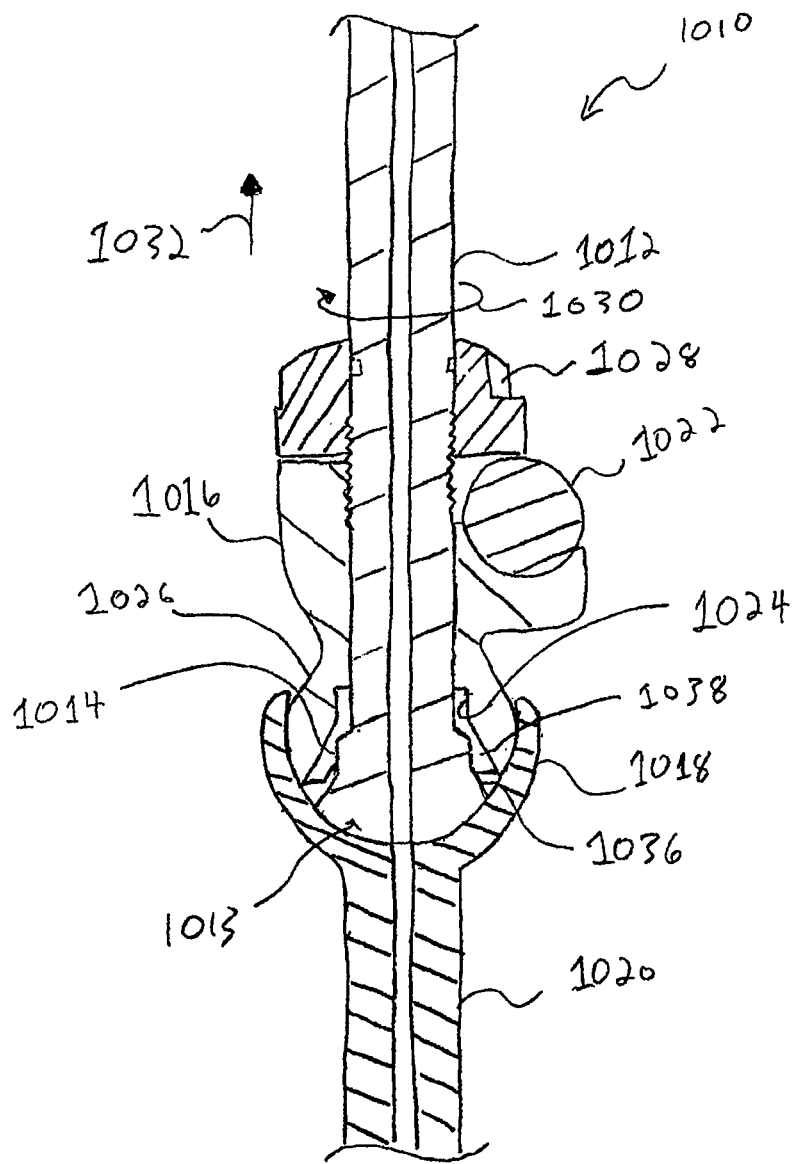
FIGS. 23-25 are cross sectional views of a spinal fixation system in accordance with another form of the present invention including the guide member of FIG. 21 and the pivot body of FIG. 22, with FIGS. 23-25 showing a process of fixing a spinal rod to a pedicle screw assembly.
Figure 24:
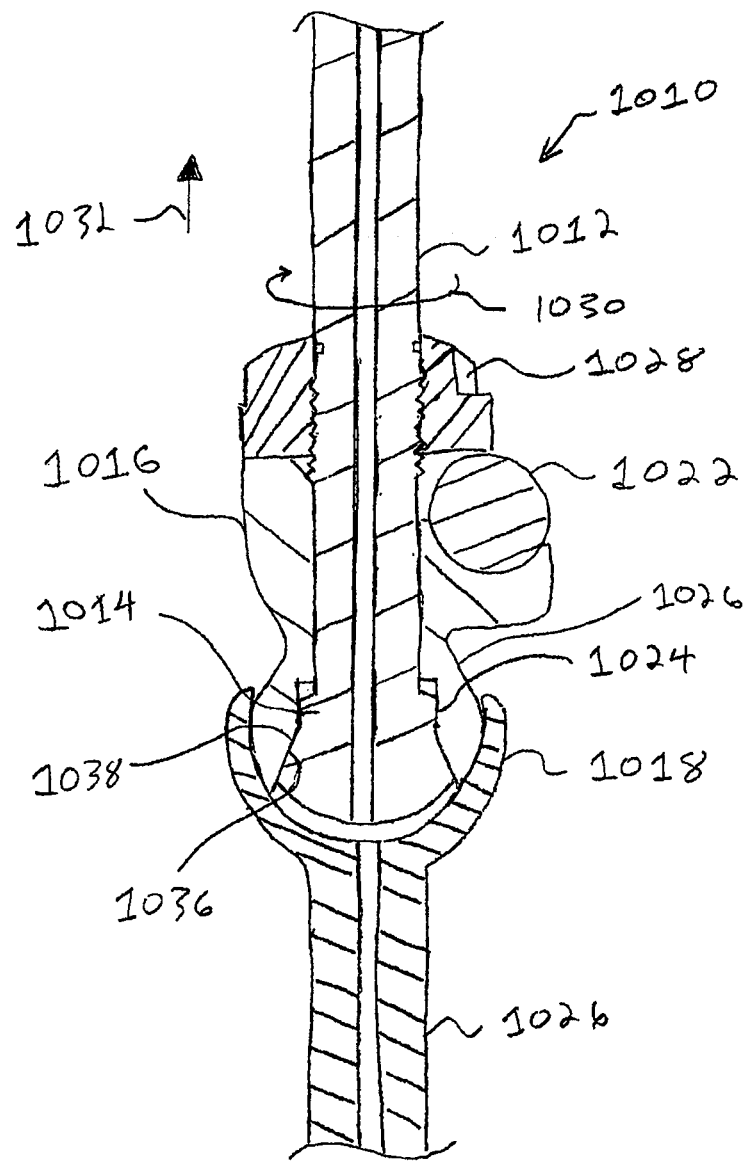
Figure 25:
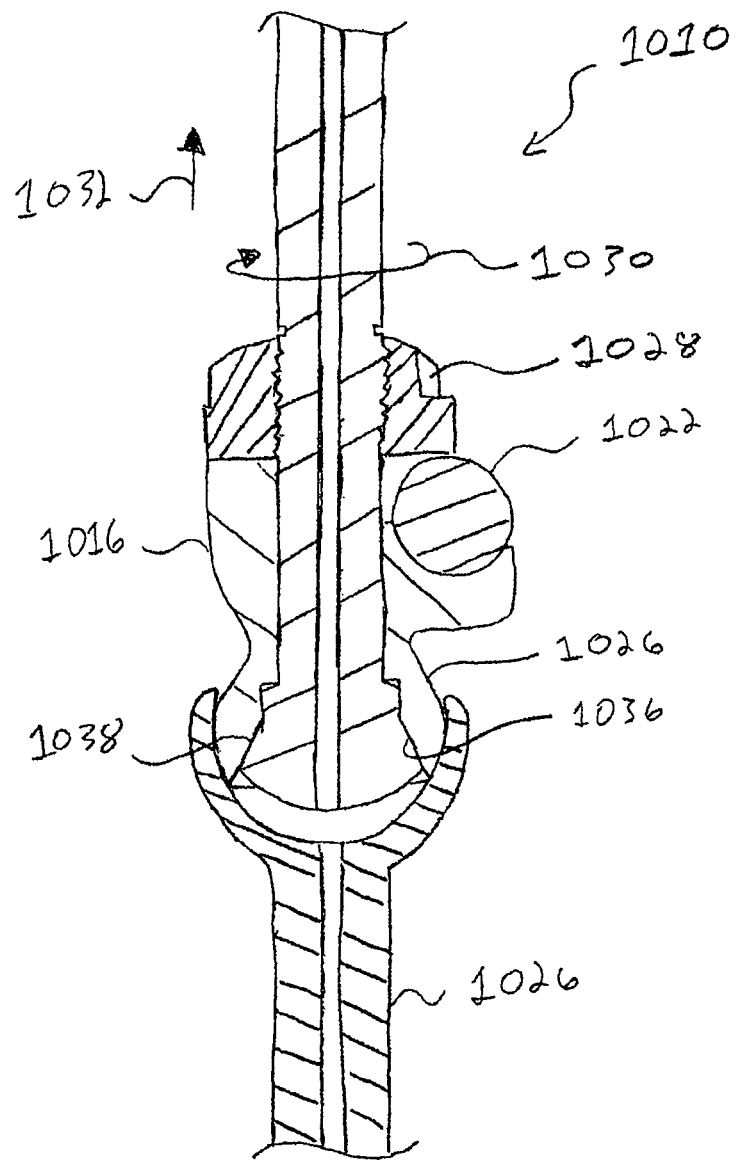

With reference to FIGS. 21-25, a spinal fixation system 1010 in accordance with another form of the present invention is disclosed. The spinal fixation system 1010 is substantially similar to the spinal fixation system 500 and FIGS. 23-25 are cross-sectional views substantially similar to FIGS. 13A and 14. One difference between the spinal fixation system 1010 and the spinal fixation system 500 is that the spinal fixation system 1010 has a guide member 1012 with a distal end 1013 comprising a cylindrical step 1014 and a tapered annular surface 1036, as shown in FIG. 21. The step 1014 engages a pivot body 1016 to provide an intermediate stage of fixation between the pivot body 1016 and a socket 1018 of a bone screw 1020. A portion of the pivot body 1016 is removed in FIG. 22 to illustrate an interior recess 1024 of the pivot body 1016. The interior recess 1024 is sized to be complimentary to the step 1014.

As shown in FIGS. 23-25, the spinal fixation system 1010 may be shifted between an initial configuration, an intermediate fixation configuration, and a final locking configuration. Initially, the pivot body 1016 is positioned on the distal end 1013 of the guide member 1012 before a plurality of resilient fingers 1026 of the pivot body 1016 and the distal end 1013 are inserted into a socket 1018 of the bone screw 1020, as shown in FIG. 23. In this initial configuration, the step 1014 and the tapered annular surface 1036 are backed off from the interior recess 1024 and an inclined surface 1038, respectively, of the pivot body 1016. This permits the fingers 1026 to deflect radially inward during insertion of the guide member distal end 1013 and the pivot body fingers 1026 into the socket 1018. Like the bone screw 520, the bone screw 1020 may have a rim sized to restrict removal of the guide member distal end 1013 and the pivot body fingers 1026 from the socket 1018. Once the guide member 1012, pivot body 1016, and bone screw 1020 have been connected together, the resulting subassembly may be inserted through a working channel and secured to a bone, as discussed above with respect to pedicle screw subassemblies 90A, 90B (see FIG. 3A).

With continued reference to FIG. 23, a spinal rod 1022 is seated upon the pivot body 1016 while the spinal fixation system 1010 is in the initial configuration. A locking cap 1028 is slid downward along the guide member 1012 and engaged with threads of the guide member 1012. The locking cap 1028 is rotated in direction 1030 to draw the locking cap 1028 toward the pivot body 1016 and concurrently draw the guide member 1012 upward in direction 1032 within the pivot body 1016. This brings the tapered annular surface 1036 of the guide member 1012 into contact with the inclined surface 1038 on the interior of the plurality of fingers 1026 and expands the fingers 1026 radially outward. Drawing the guide member 1012 upward in direction 1032 also positions the step 1014 of the guide member 1012 within the interior recess 1024 of the pivot body 1016, as shown in FIG. 24. The presence of the guide member step 1014 within the pivot body interior recess 1024 locks the plurality of fingers 1026 in a radially expanded configuration and fixes fingers 1026 against the socket 1018 of the bone screw 1020. At this point, the spinal fixation system 1010 is in the intermediate fixation configuration. Although the pivot body 1020 is generally fixed relative to the bone screw 1020 via the engagement between the plurality of fingers 1026 and the socket 1018, the spinal rod 1022 is only loosely captured on the pivot body 1016.

Continued rotation of the locking cap 1028 in direction 1030 continues to shift the spinal fixation system 1010 to the final locking configuration, as shown in FIG. 25. Specifically, continued rotation of the locking cap 1028 draws the guide member 1012 upward within the pivot body 1016 and clamps locking cap 1028 against the spinal rod 1022. At this point, the spinal rod 1022 is fixed to the pivot body 1016 and the pivot body 1016 is fixed relative to the bone screw 1020. In the illustrated approach, the spinal rod 1022 is received on the pivot body 1016 before the locking cap 1028 is used to shift the guide member 1012 to the intermediate fixation configuration. In an alternative approach, the guide member 1012 may be shifted to the intermediate fixation configuration by drawing the guide member 1012 upward within the pivot body 1016 by hand or with a tool (not shown). In this manner, the spinal fixation system 1010 may be shifted to the intermediate fixation configuration after the bone screw 1020 has been driven into a bone but before the spinal rod 1022 has been seated on the pivot body 1016.

Returning to FIGS. 15 and 16, a spinal fixation system 700 in accordance with another form of the present invention is shown. The spinal fixation system 700 is substantially similar to the spinal fixation system 500, except that the spinal fixation system 700 has a two-part locking cap 712 instead of the one-part locking cap 514 of spinal fixation system 500. More specifically, the locking cap 712 has a two-part construction including an upper portion 713 and a lower capture portion 714, the upper portion 713 being rotatable relative to the lower capture portion 714. The upper portion 713 has internal threads, e.g., threads 728 in FIG. 17A, to engage a guide member 706. As the upper portion 713 is advanced downward along the guide member 706, an arm 726 of the lower capture portion 714 engages the spinal rod 702 and directs the spinal rod 702 into a seating surface (not shown) of an arm 710. With reference to FIG. 16, the lower capture portion 714 has an opening 716 therethrough and a flat 718 that abuts a flat 720 of the guide member 706 to maintain the lower capture portion 714 in a predetermined orientation relative to the arm 710 as the locking cap 712 travels along the guide member 706. The lower capture portion 714 may also have a seat 722 that receives the locking cap 712 and a collar 724 that engages complimentary features of the upper portion 713 in a manner that connects the upper portion 713 to the lower capture portion 714 while permitting rotation of the upper portion 713 relative to the lower capture portion 714.

Figure 17A:
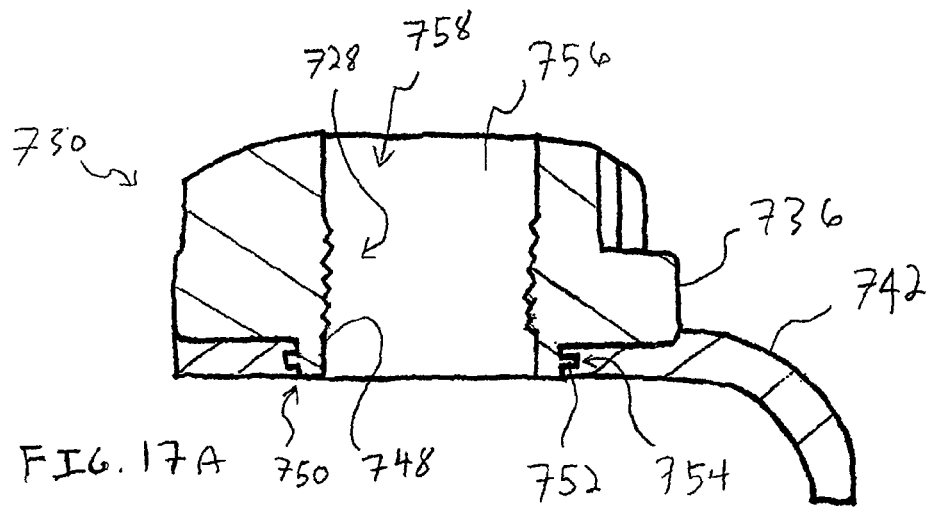
FIGS. 17A-17D are cross-sectional views of the locking cap of FIG. 15 taken along line 17-17 in FIG. 15 that illustrate alternative embodiments of a connection between an upper portion of the locking cap and the lower capture portion.

FIGS. 17A-17D show locking caps 730, 732, 734, and 790 that are similar to the locking cap 712 but illustrate alternative connections between respective upper portions 736, 738, 740, and 792 and lower capture portions 742, 744, 746, and 794. In FIG. 17A, the upper portion 736 has a neck 748 extending into an opening 750 of the lower capture portion 742. The neck 748 has a flange 752 extending outwardly into a channel 754 formed in the lower capture portion 742. The flange 752 and the channel 754 are generally annular in shape about the opening 750 so that with the flange 752 engaged within the channel 754, the upper portion 736 is rotatable relative to the lower capture portion 742. The upper portion 736 has an inner wall 756 that defines an axial passage 758 for receiving the guide member 706. In one approach, the upper portion 730 is connected to the lower capture portion 742 by pressing the neck 748 of the upper portion 736 into the opening 750 of the lower capture portion 742 until the flange 752 snaps into the channel 754.

Figure 17B:
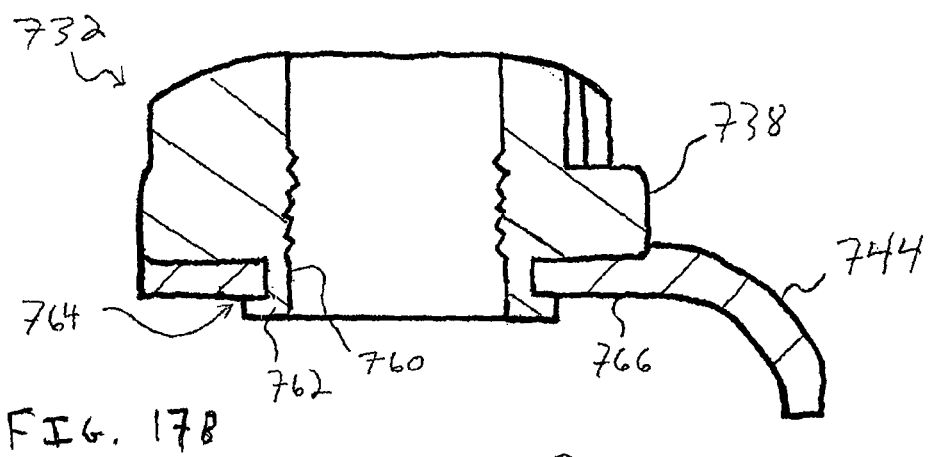

FIG. 17B shows a locking cap 732 that is similar to the locking cap 730, but the upper portion 738 has a neck 760 with a lower flange 762 for retaining the upper portion 738 on the lower capture portion 744. More specifically, the neck 760 extends through an opening 764 in the lower capture portion 744 to position the flange 762 beneath a body section 766 of the lower capture portion 744. Because the flange 762 extends below the body section 766, the pivot body 708 may have an annular cutout on the seat, i.e., seat 536 of the pivot body 508 in FIG. 12, to accommodate the flange 762 and permit the lower capture portion 744 to sit flush against the pivot body 708.

Figure 17C:
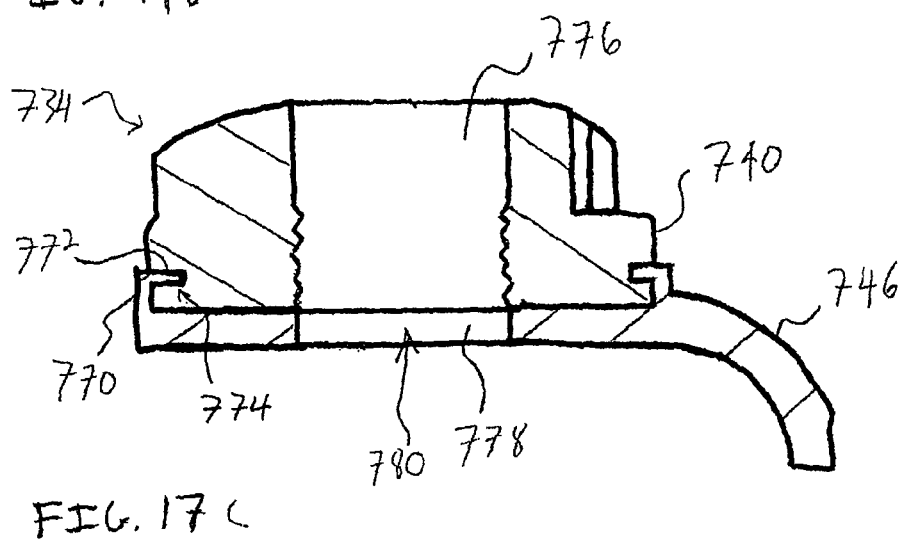

FIG. 17C shows a locking cap 734 that is similar to the locking cap 730, but the lower capture portion 746 has an upstanding wall 770 with an inwardly extending flange 772 for retaining the upper portion 740 on the lower capture portion 746. The flange 772 snaps into a complimentary channel 774 on the upper portion 740. In this embodiment, an inner wall 776 of the upper portion 740 and an inner wall 778 of the lower capture portion 746 form a passage 780 for receiving the guide member 706.

Figure 17D:
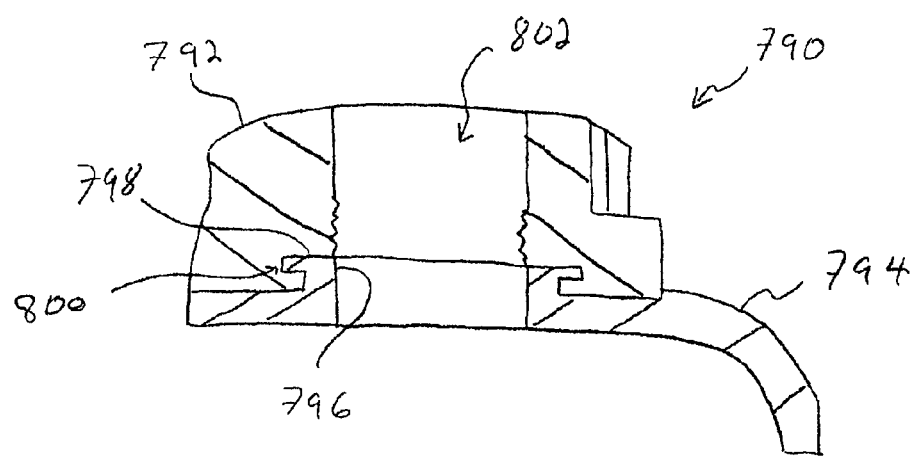

FIG. 17D shows a locking cap 790 that is similar to the locking cap 734 except that the lower capture portion 794 has an upstanding wall 796 with an outwardly extending flange 798 that snaps into a complimentary channel 800 on the upper portion 792. In this embodiment, the upstanding wall 796 forms a portion of a passage 802 for receiving the guide member 706.

Figure 18:
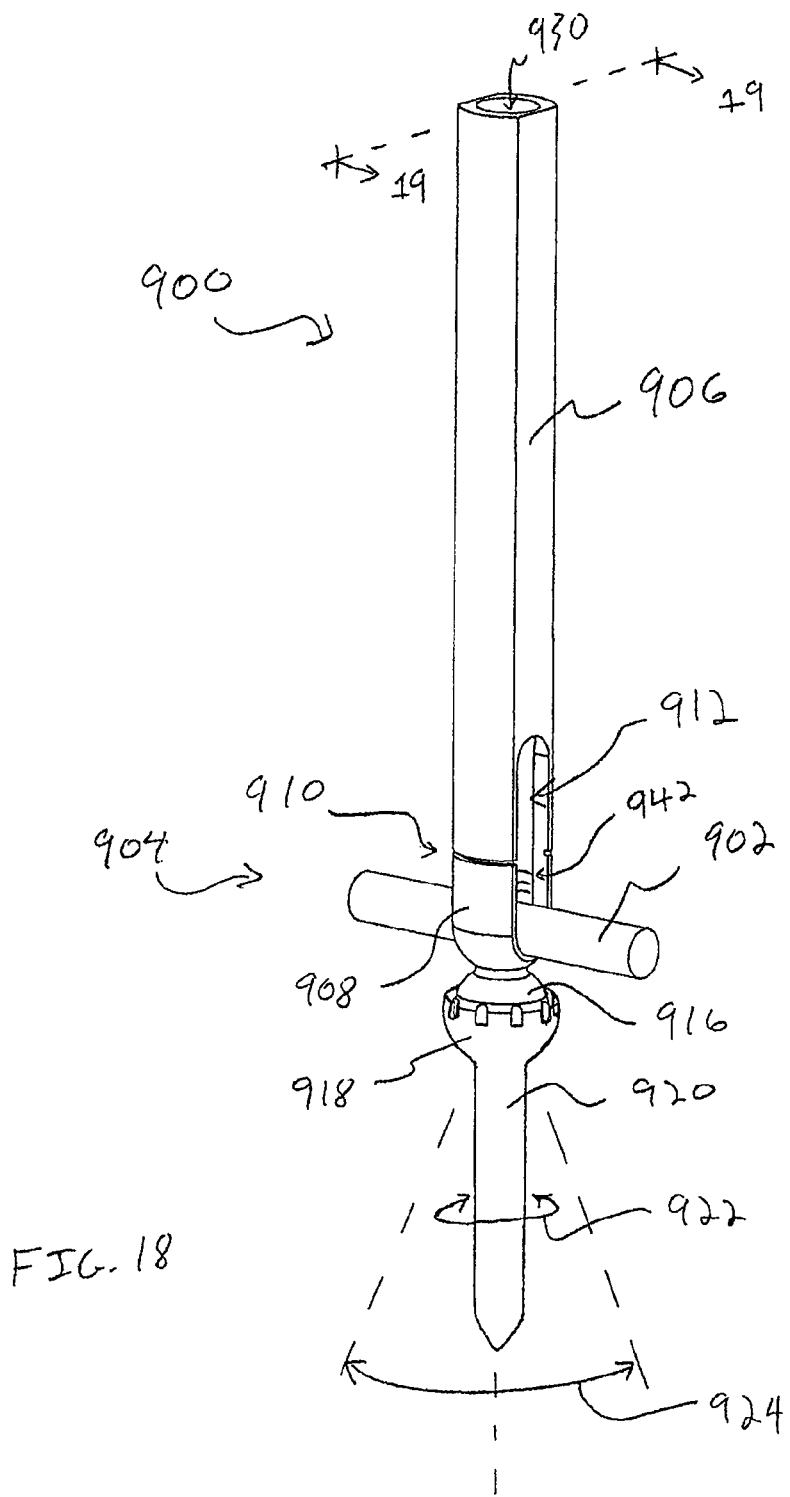
FIG. 18 is a perspective view of a spinal fixation system in accordance with another form of the present invention showing a range of motion of a bone screw of the spinal fixation system.
Figures 19, 20:
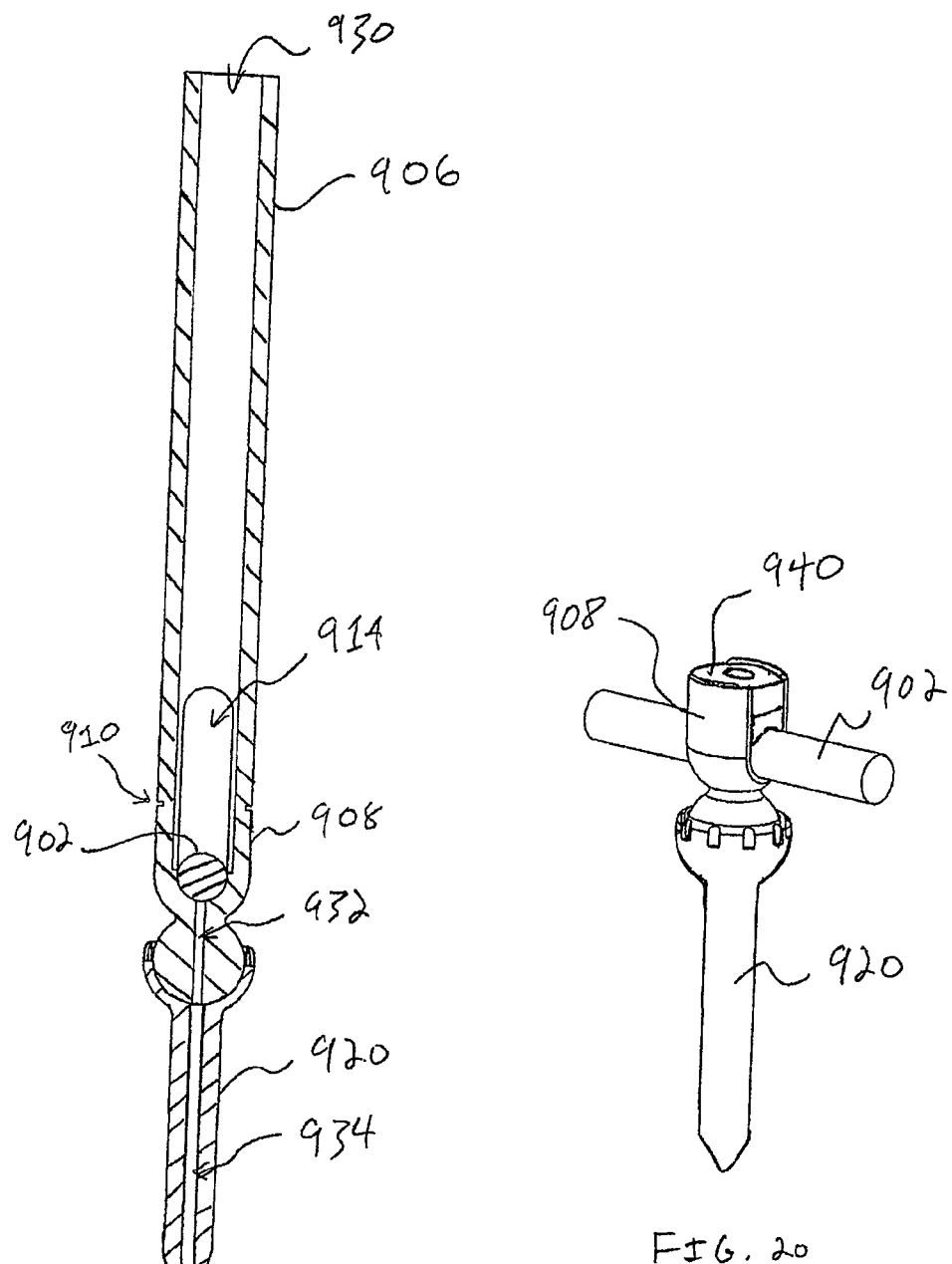
FIG. 19 is a cross-sectional view of the spinal fixation system of FIG. 18 taken across line 19-19 in FIG. 18 showing a ball-and-socket connection between a yoke of the spinal fixation system and the bone screw.
FIG. 20 is a perspective view of the spinal fixation system of FIG. 18 showing a locking cap capturing a spinal rod within the yoke.

A spinal fixation system 900 in accordance with another aspect of the present invention is illustrated in FIGS. 18-20. The spinal fixation system 900 has a ball-and-socket connection between a yoke 908 and a bone screw 920 for providing a wide range of motion between the yoke 908 and the bone screw 920 during installation of the spinal fixation system 900. The spinal fixation system 900 comprises a spinal rod 902 and a pedicle screw assembly 904 for securing the spinal rod 902 to a vertebra. The pedicle screw assembly 904 comprises a handle 906 connected to the yoke 908 via a break-off section 910, as shown in FIG. 18. The handle 906 comprises a pair of slots 912, 914 for passing the spinal rod 902 therethrough. The yoke 908 has a ball 916 sized to fit within a socket 918 of the bone screw 920. The connection between the ball 916 and the socket 918 permits the bone screw 920 to be rotated in direction 922 as well as pivoted in a range of motion as shown by arrow 924.

Turning to FIG. 19, the handle 906 has a cannula 930 for passing a locking cap 940 (see FIG. 20) therethrough into connection with threads 942 of the yoke 908. The yoke 908 may also include a cannula 932 that can be aligned with a cannula 934 of the bone screw 920 to accommodate passage of a guide wire. As shown in FIG. 20, the locking cap 940 fixes the spinal rod 902 within the yoke 908. Once the locking cap 940 has been connected to the yoke 908, a torque can be applied to the handle 906 to separate the handle 906 from the yoke 908 at the break-off section 910.

Figure 26:
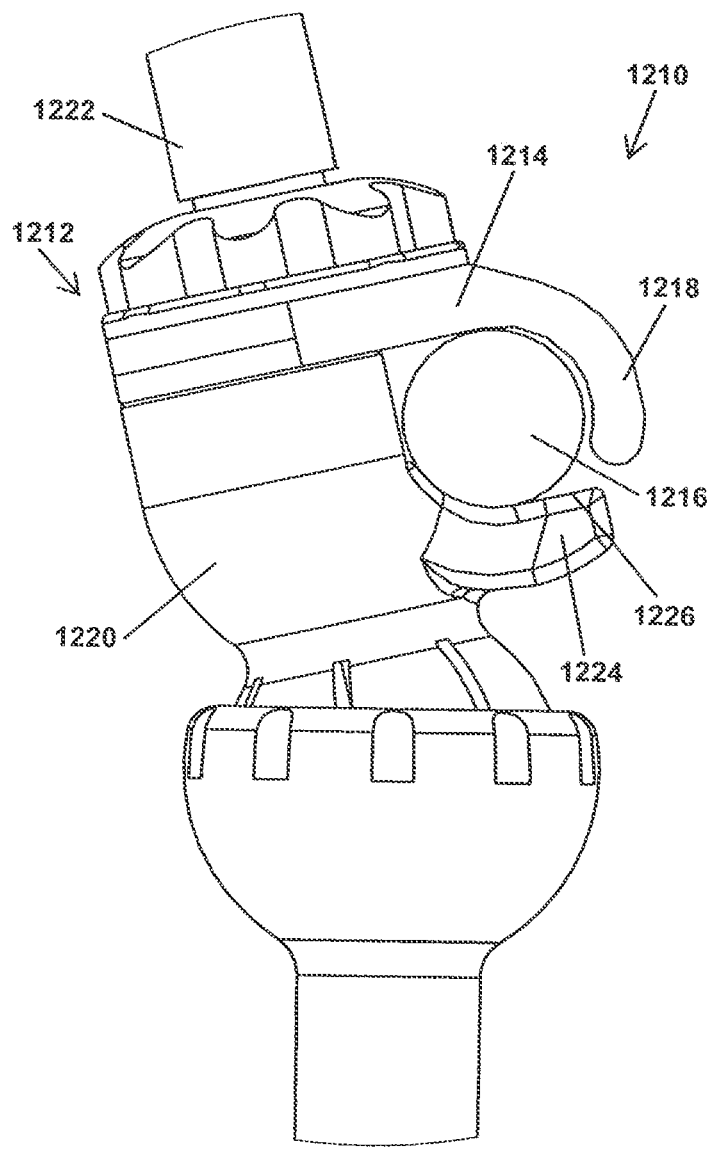
FIG. 26 is a side elevational view of a spinal fixation system in accordance with another form of the present invention showing a locking cap lower capture portion extending around a spinal rod.

A spinal fixation system 1210 in accordance with another form of the present invention is illustrated in FIG. 26. The spinal fixation system 1210 is substantially similar to the spinal fixation system 700 of FIG. 15, except that the spinal fixation system 1210 has a two-part locking cap 1212 with a lower capture portion 1214 which extends around a spinal rod 1216 a greater amount than the lower capture portion 724 extends around the spinal rod 702. More specifically, the lower capture portion 1214 has an arm 1218 that snaps onto the spinal rod 1216 and extends around an outer surface of the spinal rod 1216. If the locking cap 1212 is used to reduce the spinal rod 1216 into a pivot body 1220 of the spinal fixation system 1210, the arm 1218 may snap onto the spinal rod 1216 and hold the spinal rod 1216 close to a guide member 1222 as the locking cap 1212 and the spinal rod 1216 travel downward along the guide member 1222 toward the pivot body 1220. Another difference between the spinal fixation system 1210 and the spinal fixation system 700 is that the pivot body 1220 has an arm 1224 with a generally planar seating surface 1226 for receiving the spinal rod 1216. When the locking cap 1212 is used to fix the spinal rod 1216 to the pivot body 1220, the arm 1218 clamps the spinal rod 1216 against the seating surface 1226 of the arm 1224.

Figure 27:
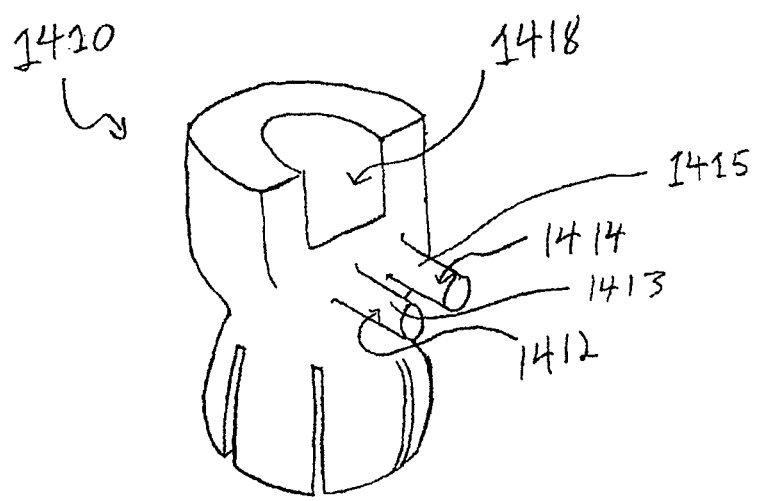
FIG. 27 is a perspective view of a pivot body similar to the pivot body of the spinal fixation system of FIG. 26.

A pivot body 1410 in accordance with another aspect of the present invention is illustrated in FIG. 27. The pivot body 1410 is substantially similar to the pivot body 1220 of FIG. 26, except that the pivot body 1410 has one or more cylindrical members 1412, 1414 for receiving the spinal rod 1216 rather than the arm 1224. In this manner, the spinal rod 1216 rests upon the convex outer seating surfaces 1413, 1415 of the cylindrical members 1412, 1414. Alternatively, the cylindrical members 1412, 1414 may have planar surfaces for receiving the spinal rod 1216. In other embodiments, the pivot body 1410 may have one or more ledges, arms, or other features for supporting the spinal rod 1216. The one or more features may have a seating surface with protrusions, raised patterns, or a generally roughened surface to engage the spinal rod 1216. If the locking cap 1212 is used to fix the spinal rod 1216 to the pivot body 1410, the arm 1218 of the lower capture portion 1214 captures the spinal rod 1216 against the pivot body 1410. Further, the spinal rod 1216 contacts a flat of the guide member 1222 via a cutout 1418 of the pivot body 1410.

Figure 28:
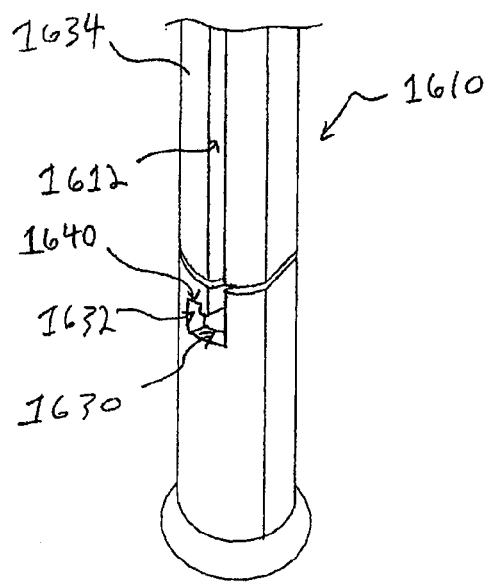
FIG. 28 is a perspective view of a guide member similar to the guide member of the spinal fixation system of FIG. 15, with FIG. 28 showing a longitudinal channel of the guide member.
Figure 29:
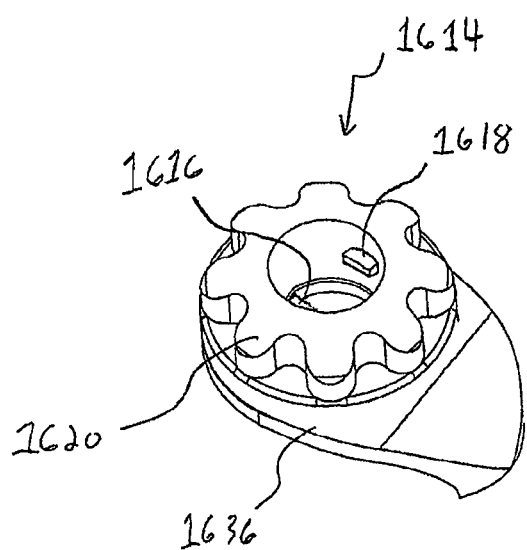
FIG. 29 is a perspective view of a locking cap for use with the guide member of FIG. 28.

A guide member 1610 in accordance with another aspect of the present invention is illustrated in FIG. 28. The guide member 1610 is substantially similar to the guide member 706 of the spinal fixation system 700 of FIG. 15, except that the guide member 1610 engages a locking cap 1614 (see FIG. 29) in a manner similar to a bayonet-style lock. More specifically, the guide member 1610 has longitudinal channels 1612 on diametrically opposed sides of the guide member 1610. The longitudinal channels 1612 are sized to receive radially projecting tabs 1616, 1618 of an upper portion 1620 of the locking cap 1614. At the end of each of the longitudinal channels 1612 is a circumferentially extending channel 1630 that leads to a vertical locking channel 1632. To engage the locking cap 1614 to the guide member 1610, the tabs 1616, 1618 are aligned with the channels 1612 and the locking cap 1614 is passed downwardly along the guide member 1610 until the tabs 1616, 1618 reach the associated circumferentially extending channel 1630. The upper portion 1620 is rotated clockwise relative to a lower capture portion 1636 of the locking cap 1614 to slide the tabs 1616, 1618 within the associated circumferentially extending channel 1630. The upper portion 1620 is rotated until the tabs 1616, 1618 reach the associated vertical locking channel 1632. In one approach, the lower capture portion 1636 may need to be compressed against the spinal rod 702 and the pivot body 708 to position the tabs 1616, 1618 within the associated circumferentially extending channel 1630. In this manner, rotating the tabs 1616, 1618 into the associated vertical locking channel 1632 allows the lower capture portion 1636, spinal rod 702, and pivot body 708 to bias the upper portion 1620 upward and the tabs 1616, 1618 into an end 1640 of the associated vertical locking channel 1632. At this point, the tabs 1616, 1618 are captured in the associated vertical locking channel 1632 and the locking cap 1614, guide member 1610, spinal rod 702, and pivot body 708 are fixed relative to one another.

It will be understood that various changes in the details, materials, and arrangements of the parts and components that have been described and illustrated in order to explain the nature of the spinal fixation system and method as described herein may be made by those skilled in the art within the principle and scope of this disclosure. Further, it will be readily appreciated by those of skill in the art the apparatuses and methods described herein may be utilized to provide fixation of bones, bone fragments, implants, and other structures besides vertebral bones.

What is claimed is:

1. A spinal fixation system for securing a spinal rod relative to a spinal bone, the system comprising:
   a bone anchor having a spherical head and a shank depending from the head, the shank extending along a longitudinal axis;
   a coupling device for being connected to the bone anchor;
   an elongate guide member of the coupling device having a proximal end portion and a distal end portion and a longitudinal axis extending therebetween, the distal end portion including a flexible socket sized for fitting about the spherical head of the bone anchor for forming a ball and socket joint therewith;
   an outer surface of the elongate guide member for engaging and guiding the spinal rod;
   a body of the coupling device having a through opening sized to receive the proximal end portion of the elongate guide member extending therethrough to permit the body to be advanced along the elongate guide member toward the distal end portion thereof;
   an upwardly open seat of the body laterally offset from the shank longitudinal axis and the elongate guide member outer surface to permit the spinal rod to be slid downward along the outer surface and received on the upwardly open seat laterally offset from the shank longitudinal axis;

a cup portion of the body configured to engage and constrict the flexible socket of the elongate guide member about the spherical bone anchor head for fixing the elongate guide member relative to the bone anchor with shifting of the body cup portion distally over the elongate guide member flexible socket;

a locking device having a through opening sized to receive the elongate guide member therethrough and permit the locking device to be guidingly advanced downward along the elongate guide member;

a capture member of the locking device for securing the spinal rod on the body seat; and mating surfaces of the elongate guide member and the locking device capture member which have a non-rotatable mating fit therebetween with the elongate guide member extending through the locking device through opening.

2. The spinal fixation system of claim 1 wherein the locking device capture member has a through opening sized to receive the elongate guide member therein and the mating surfaces include an outer surface of the elongate guide member and an inner surface of the capture member which defines at least a portion of the capture member through opening.

3. A spinal fixation system for securing a spinal rod to a spinal bone, the system comprising:

a bone anchor having a spherical head portion and a shank portion depending from the spherical head portion;

a body having a seat and a cup portion, the seat configured for receiving a spinal rod;

an elongate actuator having a proximal portion for upstanding from the body configured to permit the spinal rod to travel therealong toward the body and a distal portion having a plurality of flexible fingers defining a socket for receiving the spherical bone anchor head, the body being shiftable relative to the elongate actuator including the proximal and distal portions thereof from an initial position where the body cup portion is not fully seated on the flexible fingers which permits relative movement between the bone anchor and the body toward a locking position where the body cup portion is fully seated on the flexible fingers and constricts the flexible fingers about the spherical bone anchor head which fixes the bone anchor relative to the body;

a locking cap configured to be connected to the elongate actuator to engage the spinal rod and secure the spinal rod on the seat of the body; and wherein the elongate actuator includes a frangible portion intermediate the proximal and distal portions that is configured to permit the elongate actuator proximal portion to be separated and removed from the distal portion after fixing the bone anchor relative to the body.

4. The spinal fixation system of claim 3 wherein the elongate actuator and the locking cap have rotary locking structures configured to be engaged and shift the locking cap toward the distal portion of the elongate actuator with turning of the locking cap in a locking direction.

5. The spinal fixation system of claim 3 wherein the body has a through opening sized to receive the elongate actuator therein.

6. The spinal fixation system of claim 5 wherein the locking cap includes a through opening sized to receive the elongate actuator therein which is aligned with the through opening of the body when the locking cap is connected to the elongate actuator.

7. The spinal fixation system of claim 3 wherein the shank portion of the bone anchor extends along a longitudinal axis thereof and the seat of the body is laterally offset from the shank portion longitudinal axis to permit the spinal rod to travel along the elongate actuator proximal portion and be received on the seat laterally offset from the shank portion longitudinal axis.

8. A spinal fixation system for securing a spinal rod relative to a spinal bone, the system comprising:

a bone anchor having a head with a socket and a shank depending from the head, the shank extending along a longitudinal axis;

a coupling device for being connected to the bone anchor;

an elongate guide member of the coupling device having a longitudinal axis;

an outer surface of the elongate guide member for engaging and guiding the spinal rod;

an upwardly open seat of the coupling device laterally offset from the shank longitudinal axis and the elongate guide member outer surface to permit the spinal rod to be slid downward along the outer surface and received on the upwardly open seat laterally offset from the shank longitudinal axis; and a flexible ball portion of the coupling device that is integral with the upwardly open seat of the coupling device so that the flexible ball portion and the upwardly open seat have a one-piece construction with the flexible ball portion thereof being sized and configured to be received in the socket of the bone anchor head to form a ball and socket joint therewith;

wherein the coupling device includes a one-piece body that includes the seat and the flexible ball portion;

the body and elongate guide member include primary engagement surfaces arranged and configured such that shifting the elongate guide member from an initial position toward a locking position brings the primary engagement surfaces together which deflects the flexible ball portion outwardly against an inner surface of the bone anchor socket; and wherein the body and the elongate guide member include secondary engagement surfaces adjacent the primary engagement surfaces that are configured such that shifting the elongate guide member to an intermediate position between the initial and locking positions brings the secondary engagement surfaces together and produces an initial outward deflection of the flexible ball portion.

9. A spinal fixation system for securing a spinal rod to a spinal bone, the system comprising:

a bone anchor having a spherical head portion and a shank portion depending from the spherical head portion;

a body having a seat and a cup portion, the seat configured for receiving a spinal rod;

an elongate actuator having a proximal portion for upstanding from the body configured to permit the spinal rod to travel therealong toward the body and a distal portion having a plurality of flexible fingers defining a socket for receiving the spherical bone anchor head, the body being shiftable relative to the elongate actuator including the proximal and distal portions thereof from an initial position where the body cup portion is not fully seated on the flexible fingers which permits relative movement between the bone anchor and the body toward a locking position where the body cup portion is fully seated on the flexible fingers and constricts the flexible fingers about the spherical bone anchor head which fixes the bone anchor relative to the body; and a locking cap configured to be connected to the elongate actuator to engage the spinal rod and secure the spinal rod on the seat of the body;

wherein the body has a through opening sized to receive the elongate actuator therein; and wherein the body includes an arm that includes at least a portion of the seat with the arm extending laterally from the body through opening such that the spinal rod is positioned laterally relative to the elongate actuator on the arm.

10. A spinal fixation system for securing a spinal rod relative to a spinal bone, the system comprising:

a bone anchor having a spherical head and a shank depending from the head, the shank extending along a longitudinal axis;

a coupling device for being connected to the bone anchor;

an elongate guide member of the coupling device having a proximal end portion and a distal end portion and a longitudinal axis extending therebetween, the distal end portion including a flexible socket sized for fitting about the spherical head of the bone anchor for forming a ball and socket joint therewith;

an outer surface of the elongate guide member for engaging and guiding the spinal rod;

a body of the coupling device having a through opening sized to receive the proximal end portion of the elongate guide member extending therethrough to permit the body to be advanced along the elongate guide member toward the distal end portion thereof;

an upwardly open seat of the body laterally offset from the shank longitudinal axis and the elongate guide member outer surface to permit the spinal rod to be slid downward along the outer surface and received on the upwardly open seat laterally offset from the shank longitudinal axis;

a cup portion of the body configured to engage and constrict the flexible socket of the elongate guide member about the spherical bone anchor head for fixing the elongate guide member relative to the bone anchor with shifting of the body cup portion distally over the elongate guide member flexible socket; and wherein the upwardly open seat of the body extends about a seat axis along which the spinal rod is oriented with the spinal rod received on the upwardly open seat and the seat axis is laterally offset from the bone anchor shank longitudinal axis.

11. The spinal fixation system of claim 10 further comprising a locking device having a clamping portion configured to engage the spinal rod and an opening sized to receive the elongate guide member therethrough to allow the locking device to be advanced onto and downward along the elongate guide member to clamp the spinal rod against the body seat.

12. The spinal fixation system of claim 11 wherein the locking device has an inner portion configured to be connected to the elongate guide member and the clamping portion includes an outer clamping member extending laterally from the inner portion to clamp the spinal rod against the body seat.

13. The spinal fixation system of claim 10 wherein the body includes a lateral opening to the seat in communication with the body through opening to minimize the lateral distance between the elongate guide member and the spinal rod with the spinal rod received on the seat.

14. The spinal fixation system of claim 10 wherein the elongate guide member flexible socket and the bone anchor spherical head portion are configured to permit the elongate guide member longitudinal axis and the bone anchor shank longitudinal axis to be coaxially aligned with the flexible socket connected to the spherical head portion.

* * * * *